(12) United States Patent
Pulé et al.

(10) Patent No.: US 11,903,967 B2
(45) Date of Patent: Feb. 20, 2024

(54) METHOD OF PREPARING T CELLS WITH INCREASED ACTIVITY

(71) Applicant: AUTOLUS LIMITED, London (GB)

(72) Inventors: Martin Pulé, London (GB); Carlotta Petticone, London (GB); James Faulkner, London (GB); Ekaterini Kotsopoulou, London (GB); Emma Chan, London (GB); Richard Beswick, London (GB)

(73) Assignee: AUTOLUS LIMITED, London (GB)

( * ) Notice: Subject to any disclaimer, the term of this patent is extended or adjusted under 35 U.S.C. 154(b) by 297 days.

(21) Appl. No.: 16/188,185

(22) Filed: Nov. 12, 2018

(65) Prior Publication Data
US 2019/0209612 A1 Jul. 11, 2019

(51) Int. Cl.
| | | |
|---|---|---|
| A61K 35/17 | (2015.01) | |
| C12N 15/85 | (2006.01) | |
| A61K 38/17 | (2006.01) | |
| A61P 35/02 | (2006.01) | |
| C12N 5/0783 | (2010.01) | |
| C12N 5/00 | (2006.01) | |
| C07K 14/725 | (2006.01) | |

(52) U.S. Cl.
CPC ............ *A61K 35/17* (2013.01); *A61K 38/177* (2013.01); *A61P 35/02* (2018.01); *C12N 5/0087* (2013.01); *C12N 5/0636* (2013.01); *C12N 5/0638* (2013.01); *C12N 15/8509* (2013.01); *C07K 14/7051* (2013.01); *C12N 2015/8518* (2013.01); *C12N 2501/599* (2013.01); *C12N 2510/00* (2013.01); *C12N 2810/6054* (2013.01); *C12N 2810/6081* (2013.01)

(58) Field of Classification Search
CPC ....... A61K 35/17; A61K 38/177; A61P 35/02; C12N 5/0087; C12N 5/0636; C12N 5/0638; C12N 15/8509; C12N 2015/8518; C12N 2501/599; C12N 2510/00; C12N 2810/6054; C12N 2810/6081; C07K 14/7051
See application file for complete search history.

(56) References Cited

U.S. PATENT DOCUMENTS

| | | |
|---|---|---|
| 7,052,906 B1 | 5/2006 | Lawson et al. |
| 7,131,958 B2 | 11/2006 | Deverre |
| 7,147,626 B2 | 12/2006 | Goodman et al. |
| 2017/0034998 A1 | 2/2017 | Marchesan |
| 2017/0066827 A1 | 3/2017 | Pule et al. |

FOREIGN PATENT DOCUMENTS

| | | | |
|---|---|---|---|
| WO | WO-2003/093318 A1 | 11/2003 | |
| WO | WO-2013/074916 A1 | 5/2013 | |
| WO | WO-2015/132598 A1 | 9/2015 | |
| WO | WO-2015132598 A1 * | 9/2015 | ............ A61P 35/02 |
| WO | WO-2016/154628 A1 | 9/2016 | |
| WO | WO-2017/015490 A1 | 1/2017 | |
| WO | WO-2017/117112 A1 | 7/2017 | |
| WO | WO-2018/224844 A1 | 12/2018 | |

OTHER PUBLICATIONS

Maciocia, PM., Wawrzyniecka, P., Philip, B., et al. Targeting T-Cell Receptor β-Constant Domain for Immunotherapy of T-Cell Malignancies. Blood, 2016; 128(22): 811; Abstract, 58th ASH Annual Meeting, Session 703: Adoptive Immunotherapy II ( Year: 2016).*
Gomes-Silva, D., Srinivasan, M., Sharma, S., et al. CD7-edited T cells expressing a CD7-specific CAR for the therapy of T-cell malignancies. Blood 2017; 130 (3): 285-296 (Year: 2017).*
Kochenderfer, JN.; Feldman, SA.; Zhao, Y., et al. Construction and Preclinical Evaluation of an Anti-CD19 Chimeric Antigen Receptor, Journal of Immunotherapy, 2009; 32(7): 689-702 (Year: 2009).*
Maciocia PM, Wawrzyniecka PA, Philip B, Ricciardelli I, Akarca AU, Onuoha SC, Legut M, Cole DK, Sewell AK, Gritti G, Somja J. Targeting the T cell receptor β-chain constant region for immunotherapy of T cell malignancies. Nature medicine. Dec. 2017;23(12): 1416-23; cited in IDS dated Jul. 18, 2019 (Year: 2017).*
Song DG, Ye Q, Poussin M, Liu L, Figini M, Powell Jr DJ. A fully human chimeric antigen receptor with potent activity against cancer cells but reduced risk for off-tumor toxicity. Oncotarget. Aug. 28, 2015;6(25):21533. (Year: 2015).*
Prosser ME, Brown CE, Shami AF, Forman SJ, Jensen MC. Tumor PD-L1 co-stimulates primary human CD8+ cytotoxic T cells modified to express a PD1: CD28 chimeric receptor. Molecular immunology. Jul. 1, 2012;51(3-4):263-72. (Year: 2012).*
International Search Report and Written Opinion from corresponding International Application No. PCT/GB2015/050643 dated Jul. 9, 2015.
Maciocia et al, "Targeting the T cell receptor beta-chain constant region for immunotherapy of T cell malignancies," Nature Medicine 23(12):1416-1423 (2017).
Maciocia et al, "Targeting T-Cell Receptor ß-Constant Domain for Immunotherapy of T-Cell Malignancies," Blood 128:811 (2016).
US-2017-0334998 U.S. Appl. No. 15/606,480, filed May 26, 2017.
US-2017-0066827 U.S. Appl. No. 15/123,287, filed Sep. 2, 2016.
U.S. Appl. No. 16/229,684, filed Dec. 21, 2018.
Sandrin et al., Lentiviral vectors pseudotyped with a modified RD114 envelope glycoprotein show increased stability in sera and augmented transduction of primary lymphocytes and CD34+ cells derived from human and nonhuman primates, Blood 100(3)823-832 (2002).

* cited by examiner

*Primary Examiner* — Robert M Kelly

(57) ABSTRACT

The present invention provides a method of preparing a population of genetically modified cells which comprise a chimeric antigen receptor (CAR) or a transgenic T-cell receptor (TCR) comprising: providing a starting population of cells; depleting said starting population of cells which express a target antigen; and introducing into a cell in the depleted starting population a nucleic acid sequence which encodes a CAR or transgenic TCR against the target antigen. The present invention also provides genetically modified cells, pharmaceutical compositions and pharmaceutical compositions for use in the treatment and/or prevention of disease.

7 Claims, 10 Drawing Sheets

METHOD OF PREPARING T CELLS WITH INCREASED ACTIVITY

FIELD OF THE INVENTION

The present invention relates to a method of preparing a population of genetically modified cells which comprise a chimeric antigen receptor (CAR) or a transgenic T-cell receptor (TCR). The method comprises depleting cells which express a target antigen of a CAR or transgenic TCR. The present invention further relates to a genetically modified cell or population of genetically modified cells obtainable by the method of the present invention. The present invention also provides pharmaceutical compositions comprising the genetically modified cell(s) and their use in treating and/or preventing a disease.

BACKGROUND TO THE INVENTION

Adoptive cell therapy (ACT) is a personalised therapy that involves administration to the subject of immune cells with activity directed against a specific disease related antigen. ACT using naturally occurring tumour-reactive lymphocytes or tumour-infiltrating lymphocytes (TILs) has mediated durable, complete regressions in patients with melanoma. However, melanoma appears to be the only cancer which reproducibly gives rise to TIL cultures capable of specific antitumor recognition and reactivity.

Subsequent approaches have sought to more widely apply ACT to treat other diseases and cancers by genetically engineering cells to express anti-tumour receptors. For example, TCRs are composed of one α and one β chain. These receptors recognise antigens that have been processed and presented by an MHC molecule. Normal circulating lymphocytes transduced with a retrovirus encoding a TCR that recognized the MART-1 melanoma-melanocyte antigen have been shown to mediate tumour regression.

Another approach is the administration of lymphocytes genetically expressed to express a CAR. CARs are artificial receptors that can be constructed by linking the variable regions of the antibody heavy and light chains to intracellular signalling chains alone or in combination with other signalling moieties. CARs recognise antigens which are presented on the tumour cell surface, but do not need to be MHC-restricted. For example, CARs against the B cell antigen CD19 have been shown to mediate regression of an advanced B cell lymphoma.

An essential material in the manufacture of genetically modified cell therapies is the starting material i.e. the cells which will be genetically modified. These cells may be obtained from the patient in case of autologous therapies or from a different donor in case of allogeneic therapies. These cells may be obtained from peripheral blood or leukapheresate e.g. from the patient to be treated (autologous) or a different donor (allogeneic).

There remains a need for improved methods for the production of genetically modified cells which provide reproducible efficiency and/or enhanced safety and/or which avoid the manufacture of cell populations and/or pharmaceutical compositions inadequate for administration to a patient, thereby preventing subsequent delays in treatment.

SUMMARY OF ASPECTS OF THE INVENTION

Figure 1:
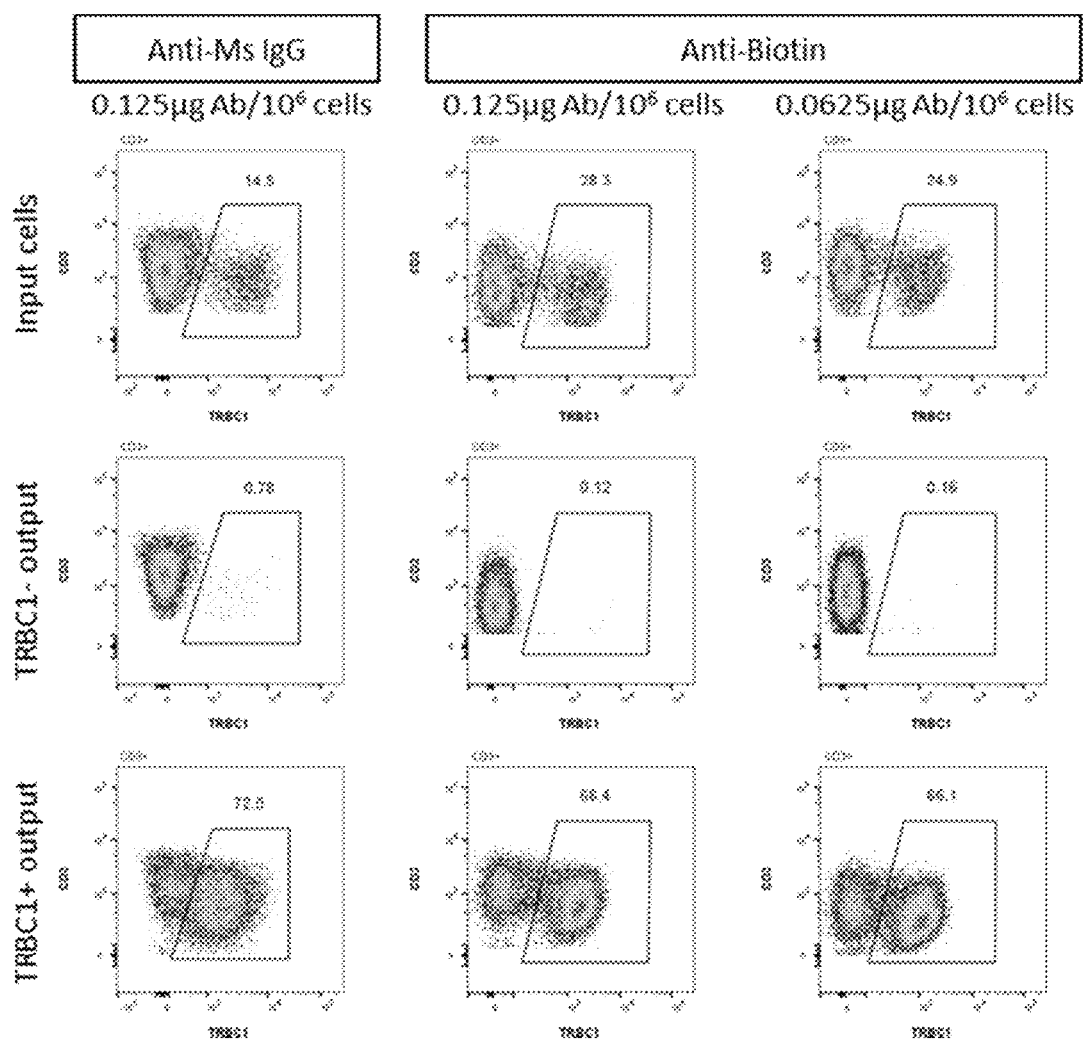
FIG. 1—Fluorescence activated cell sorting (FACS) plots showing TRBC1 cell depletion. Representative depletions performed with unconjugated antibody/anti-Ms IgG microbeads or biotinylated antibody/anti-biotin microbeads as indicated. The plots show TRBC1+ cell content in the non depleted input, TRBC1− output (depleted column flow through) and TRBC1+ output (column captured) samples from depletions performed on $2.1 \times 10^7$.

The present inventors provide a method for preparing a population of genetically modified cells which comprise a CAR or a transgenic TCR.

The present inventors have shown that depleting a population of cells which express a target antigen during manufacture results in an improved genetically modified cell product wherein the genetically modified cells express a CAR or transgenic TCR against the target antigen. An advantage of the present invention is that genetically modified cells produced by this method are less exhausted and less differentiated, more naive than genetically modified cells produced without depletion of cells expressing the target antigen. Without wishing to be bound by theory, the significant percentage of undifferentiated cells and low number of cells positive for multiple exhaustion markers indicate that the genetically modified cells of the present invention or produced by methods of the present invention should have improved in vivo persistence post administration and/or improved cytolytic activity post administration.

Another advantage of the present invention is that genetically modified cells produced by the method are more uniformly genetically modified. There is less variation between methods performed on cell populations from different donors and between cell preparations and/or pharmaceutical compositions.

Advantageously, when compared with methods which do not comprise a depletion step, the method according to the present invention produces a population of genetically modified cells which are more pure and contain low or undetectable levels of cells which express the target antigen. The method according to the present invention minimises or eliminates the risk of genetically modifying cells which express the target antigen. This may provide an added safety benefit in the case where the target cells (i.e. cells expressing the target antigen) are cancer cells.

Furthermore, the method according to the present invention reduces failures in transduction or transfection when a high proportion of cells which express the target antigen are present in the source of cells e.g. the starting population of cells.

Without wishing to be bound by theory, the depletion of cells expressing target antigen may reduce differentiation and/or exhaustion of cells, due to fratricide by cells expressing a CAR or transduced TCR against the target antigen during manufacture (e.g. during the cell expansion phase).

In one aspect the invention provides a method of preparing a population of genetically modified cells which comprise a chimeric antigen receptor (CAR) or a transgenic T-cell receptor (TCR) comprising:
(i) providing a starting population of cells;
(ii) depleting said starting population of cells which express a target antigen; and
(iii) introducing into a cell in the depleted starting population a nucleic acid sequence which encodes a CAR or transgenic TCR against the target antigen.

The CAR or transgenic TCR may be introduced to a cytolytic immune cell in accordance with the present invention. Suitably the CAR or transgenic TCR may be introduced into a T cell in accordance with the present invention.

The starting population of cells in the method of the present invention may comprise a leukapheresate.

The starting population of cells in the method of the present invention may comprise peripheral blood mononuclear cells (PBMCs).

The depleted starting population in the method of the present invention may comprise PBMCs.

The depleted starting population in the method of the present invention may comprise cytolytic immune cells.

The depleted starting population in the method of the present invention may comprise T cells.

The target antigen in the method of the present invention may be TCR beta constant region 1 (TRBC1).

The target antigen in the method of the present invention may be TCR beta constant region 2 (TRBC2).

In one embodiment the percentage of CAR or transgenic TCR target antigen positive cells may be lower in the population of transduced or transfected cells than in the starting population. Suitably, fewer than 10% of the transduced or transfected cells may express the target antigen of the CAR or transgenic TCR. Suitably, fewer than 5% of the transduced or transfected cells may express the target antigen of the CAR or transgenic TCR. Suitably, less than 1% of the transduced or transfected cells may express the target antigen of the CAR or transgenic TCR.

In one embodiment the percentage of CAR or transgenic TCR target antigen positive cells may be lower in the population of genetically modified cells than in the starting population. Suitably, fewer than 10% of the genetically modified cells may express the target antigen of the CAR or transgenic TCR. Suitably, fewer than 5% of the genetically modified cells may express the target antigen of the CAR or transgenic TCR. Suitably, less than 1% of the genetically modified cells may express the target antigen of the CAR or transgenic TCR.

Suitably, the population of transduced or transfected cells may be prepared as a pharmaceutical composition.

Suitably, the population of genetically modified cells may be prepared as a pharmaceutical composition.

In a further aspect the present invention provides a genetically modified cell comprising a CAR or transgenic TCR obtainable (suitably obtained) by the method of the present invention.

Suitably, the present invention provides a population of genetically modified cells according to the present invention, or a population of genetically modified cells obtainable (suitably obtained) by the method of the present invention.

Suitably, the population of genetically modified cells in accordance with the present invention may comprise cytolytic immune cells.

Suitably, the population of genetically modified cells in accordance with the present invention may comprise T cells.

Suitably, genetically modified cells according to the present invention may be less differentiated or more naive than genetically modified cells prepared without depleting cells which express the target antigen of the CAR or transgenic TCR.

The genetically modified cells according to the present invention may have increased expression of CD27 and/or CD62L compared with genetically modified cells prepared without depleting cells which express the target antigen of the CAR or transgenic TCR.

Suitably, the genetically modified cells according to the present invention may be more naïve than genetically modified cells prepared without depleting cells which express the target antigen of the CAR or transgenic TCR.

Suitably, the genetically modified cells according to the present invention may be less exhausted compared with genetically modified cells prepared without depleting cells which express the target antigen of the CAR or transgenic TCR.

The genetically modified cells in accordance with the present invention may have decreased expression of one or more exhaustion markers compared with genetically modified cells prepared without depleting cells which express the target antigen of the CAR or transgenic TCR.

The one or more exhaustion markers may be selected from the group consisting of: PD1, Lag3 and Tim3.

In a further aspect the present invention provides a pharmaceutical composition which comprises a population of genetically modified cells according to the present invention or obtainable (preferably obtained) by a method according to the present invention.

In one aspect the present invention provides a pharmaceutical composition according to the present invention, for use in treating and/or preventing a disease.

In another aspect the present invention provides a method for treating and/or preventing a disease, which comprises the step of administering a pharmaceutical composition according to the present invention to a subject in need thereof.

The method for treating and/or preventing a disease may further comprise the following steps:
  providing a sample comprising a starting population of cells;
  (ii) depleting said starting population of cells which express a target antigen;
  (iii) introducing into a cell in the depleted starting population a nucleic acid sequence which encodes a CAR or transgenic TCR against the target antigen; and
  (iv) administering the cells from (iii) to a subject.

Suitably, the method may additionally comprise a cell expansion step before administration to the patient e.g. the cells may be cultured before administration to the patient.

The cell in accordance with the present invention may be autologous. The cell in accordance with the present invention may be allogeneic.

The cell in accordance with the present invention may be isolated from a subject.

In a further aspect the present invention relates to the use of a pharmaceutical composition according to the present invention in the manufacture of a medicament for the treatment and/or prevention of a disease.

In one embodiment, the disease may be cancer. In one embodiment the cancer may be a solid tumour cancer.

In one embodiment the disease may be a haematological malignancy. Suitably, the disease may be a leukaemia. Suitably, the disease may be a lymphoma.

In a further aspect the present invention provides a kit comprising:
  (i) a first nucleic acid sequence which encodes a CAR or a transgenic TCR; and
  (ii) means for depleting cells expressing the target antigen for the CAR or transgenic TCR.

In one aspect the present invention provides a method of reducing the number of cells in a pharmaceutical composition which express a target antigen and express a CAR or transgenic TCR against the target antigen comprising:
  providing a starting population of cells;
  depleting said starting population of cells which express a target antigen;
  introducing into a cell in the depleted starting population a nucleic acid which encodes a CAR or transgenic TCR against the target antigen; and
  incorporating the cells into a pharmaceutical composition.

The cells may be expanded prior to incorporation into a pharmaceutical composition.

The cells may be activated prior to the introduction of a nucleic acid which encodes a CAR or transgenic TCR.

The starting population of cells may have previously been frozen and thawed prior to depletion of cells which express a target antigen.

The CAR or transgenic TCR may be introduced into the cell by transduction, for example using a retroviral or lentiviral vector, and the multiplicity of infection may be selected to be sufficient to transduce cells which do not express the target antigen and insufficient to transduce cells which express the target antigen.

The percentage of CAR or transgenic TCR target antigen positive cells may be lower in the pharmaceutical composition than in the starting population of cells. Fewer than 10% of the cells in the pharmaceutical composition may express the target antigen of the CAR or transgenic TCR. Fewer than 5% of the cells in the pharmaceutical composition may express the target antigen of the CAR or transgenic TCR. Less than 1% of the cells in the pharmaceutical composition may express the target antigen of the CAR or transgenic TCR.

Fewer than 5% of the genetically modified cells in the pharmaceutical composition may express the target antigen. Fewer than 2% of the genetically modified cells in the pharmaceutical composition may express the target antigen. Less than 1% of the genetically modified cells in the pharmaceutical composition may express the target antigen.

DETAILED DESCRIPTION

The present invention provides a method of preparing a population of genetically modified cells which comprise a chimeric antigen receptor or transgenic T cell receptor. The method comprises depletion of cells which express a target antigen and introduction of a nucleic acid sequence which encodes a CAR or transgenic TCR against the target antigen. The genetically modified cells are useful in methods for treating and/or preventing disease. By administering the genetically modified cells to the subject, the genetically modified cells cause depletion of cells expressing the target antigen.

Chimeric Antigen Receptor (CAR)

A classical chimeric antigen receptor (CAR) is a chimeric type I trans-membrane protein which connects an extracellular antigen-recognizing domain (binder) to an intracellular signalling domain (endodomain). The binder is typically a single-chain variable fragment (scFv) derived from a monoclonal antibody (mAb), but it can be based on other formats which comprise an antibody-like antigen binding site. A spacer domain is usually necessary to isolate the binder from the membrane and to allow it a suitable orientation. A common spacer domain used is the Fc of IgG1. More compact spacers can suffice e.g. the stalk from CD8α and even just the IgG1 hinge alone, depending on the antigen. A trans-membrane domain anchors the protein in the cell membrane and connects the spacer to the endodomain.

Early CAR designs had endodomains derived from the intracellular parts of either the γ chain of the FcεR1 or CD3ζ. Consequently, these first generation receptors transmitted immunological signal 1, which was sufficient to trigger T-cell killing of cognate target cells but failed to fully activate the T-cell to proliferate and survive. To overcome this limitation, compound endodomains have been constructed: fusion of the intracellular part of a T-cell co-stimulatory molecule to that of CD3ζ results in second generation receptors which can transmit an activating and co-stimulatory signal simultaneously after antigen recognition. The co-stimulatory domain most commonly used is that of CD28. This supplies the most potent co-stimulatory signal—namely immunological signal 2, which triggers T-cell proliferation. Some receptors have also been described which include TNF receptor family endodomains, such as the closely related OX40 and 41BB which transmit survival signals. Even more potent third generation CARs have now been described which have endodomains capable of transmitting activation, proliferation and survival signals.

CAR-encoding nucleic acids may be transferred to T cells using, for example, retroviral vectors. Lentiviral vectors may be employed. In this way, a large number of antigen-specific cells can be generated for adoptive cell transfer. When a CAR binds the target-antigen, this results in the transmission of an activating signal to the T-cell it is expressed on. Thus the CAR directs the specificity and cytotoxicity of the T cell towards tumour cells expressing the targeted antigen.

CARs typically therefore comprise: (i) an antigen-binding domain; (ii) a spacer; (iii) a transmembrane domain; and (iii) an intracellular domain which comprises or associates with a signalling domain.

Antigen Binding Domain

The antigen binding domain is the portion of the CAR or transgenic TCR which recognizes antigen.

Numerous antigen-binding domains are known in the art, including those based on the antigen binding site of an antibody, antibody mimetics, and T-cell receptors. For example, the antigen-binding domain may comprise: a single-chain variable fragment (scFv) derived from a monoclonal antibody; a natural ligand of the target antigen; a peptide with sufficient affinity for the target; a single domain antibody; an artificial single binder such as a Darpin (designed ankyrin repeat protein); or a single-chain derived from a T-cell receptor.

The antigen binding domain may comprise a domain which is not based on the antigen binding site of an antibody. For example the antigen binding domain may comprise a domain based on a protein/peptide which is a soluble ligand for a tumour cell surface receptor (e.g. a soluble peptide such as a cytokine or a chemokine); or an extracellular domain of a membrane anchored ligand or a receptor for which the binding pair counterpart is expressed on the tumour cell.

The antigen binding domain may be based on a natural ligand of the antigen.

The antigen binding domain may comprise an affinity peptide from a combinatorial library or a de novo designed affinity protein/peptide.

Spacer Domain

The CAR may comprise a spacer sequence to connect the antigen-binding domain with the transmembrane domain and spatially separate the antigen-binding domain from the endodomain. A flexible spacer allows the antigen-binding domain to orient in different directions to facilitate binding.

The spacer sequence may, for example, comprise an IgG1 Fc region, an IgG1 hinge or a human CD8 stalk or the mouse CD8 stalk. The spacer may alternatively comprise an alternative linker sequence which has similar length and/or domain spacing properties as an IgG1 Fc region, an IgG1 hinge or a CD8 stalk. A human IgG1 spacer may be altered to remove Fc binding motifs.

Transmembrane Domain

The transmembrane domain is the sequence of the CAR that spans the membrane.

A transmembrane domain may be any protein structure which is thermodynamically stable in a membrane. This is typically an alpha helix comprising of several hydrophobic residues. The transmembrane domain of any transmembrane protein can be used to supply the transmembrane portion of the invention.

The presence and span of a transmembrane domain of a protein can be predicted by those skilled in the art using bioinformatics tools such as the TMHMM algorithm (www.cbs.dtu.dk/services/TMHMM-2.0/). Further, given that the transmembrane domain of a protein is a relatively simple structure, i.e. a polypeptide sequence predicted to form a hydrophobic alpha helix of sufficient length to span the membrane, an artificially designed TM domain may also be used (for example as described in U.S. Pat. No. 7,052,906 B1 which is incorporated herein by reference).

The transmembrane domain may be derived from CD28, which gives good receptor stability.

Activating Endodomain

The endodomain is the signal-transmission portion of the CAR. It may be part of or associate with the intracellular domain of the CAR. After antigen recognition, receptors cluster, native CD45 and CD148 are excluded from the synapse and a signal is transmitted to the cell. The most commonly used endodomain component is that of CD3-zeta which contains 3 ITAMs. This transmits an activation signal to the T cell after antigen is bound. CD3-zeta may not provide a fully competent activation signal and additional co-stimulatory signalling may be needed. For example, chimeric CD28 and OX40 can be used with CD3-Zeta to transmit a proliferative/survival signal, or all three can be used together.

Where a CAR comprises an activating endodomain, it may comprise the CD3-Zeta endodomain alone, the CD3-Zeta endodomain with that of either CD28 or OX40 or the CD28 endodomain and OX40 and CD3-Zeta endodomain.

Any endodomain which contains an ITAM motif can act as an activation endodomain.

Transgenic T-Cell Receptor (TCR)

The T-cell receptor (TCR) is a molecule found on the surface of T cells which is responsible for recognizing fragments of target antigen as peptides bound to major histocompatibility complex (MHC) molecules.

The TCR is a heterodimer composed of two different protein chains. In humans, in 95% of T cells the TCR consists of an alpha (a) chain and a beta 03) chain (encoded by TRA and TRB, respectively), whereas in 5% of T cells the TCR consists of gamma and delta (γ/δ) chains (encoded by TRG and TRD, respectively).

Each chain is composed of two extracellular domains: a variable (V) region and a constant (C) region. The constant region is proximal to the cell membrane, followed by a transmembrane region and a short cytoplasmic tail, while the Variable region binds to the peptide/MHC complex. The variable domain of the TCR α-chain and β-chain each have three hypervariable or complementarity determining regions (CDRs). CDR3 is the main CDR responsible for recognizing processed antigen. The constant domain of the TCR consists of short connecting sequences in which a cysteine residue forms disulphide bonds, which form a link between the two chains.

When the TCR engages with antigenic peptide and MHC (peptide/MHC), the T lymphocyte is activated through signal transduction.

In contrast to conventional antibody-directed target antigens, antigens recognized by the TCR can include the entire array of potential intracellular proteins, which are processed and delivered to the cell surface as a peptide/MHC complex.

It is possible to engineer cells to express heterologous (i.e. non-native) TCR molecules by artificially introducing the TRA and TRB genes; or TRG and TRD genes into the cell using a vector. Such 'heterologous' TCRs may also be referred to herein as 'transgenic TCRs'. For example, the genes for genetically modified TCRs may be reintroduced into autologous T cells and transferred back into patients for T cell adoptive therapies.

Target Antigen

A "target antigen" as used herein refers to the antigen which the CAR or transgenic TCR has specificity for, i.e. the antigen which the antigen binding domain of the CAR or transgenic TCR has been engineered to have specificity for.

A target antigen may be a disease associated antigen.

Suitably the target antigen may be associated with chronic infection.

Suitably the target antigen may be associated with autoimmunity.

A target antigen may be a tumour associated antigen e.g. a cancer related antigen.

Various target antigens are known, as shown in the following table. The antigen-binding domain used in the present invention may be a domain which is capable of binding an antigen as indicated therein.

| Disease | Target antigen |
| --- | --- |
| T cell lymphoma/T cell leukaemia | TCR beta constant region 1 (TRBC1) |
| T cell lymphoma/T cell leukaemia | TCR beta constant region 2 (TRBC2) |
| Diffuse Large B-cell Lymphoma | CD19, CD20, CD22 |
| Breast cancer | ErbB2, MUC1 |
| AML | CD13, CD33 |
| ALL | CD19, CD22 |
| Neuroblastoma | GD2, NCAM, ALK, GD2 |
| B-CLL | CD19, CD52, CD160 |
| Colorectal cancer | Folate binding protein, CA-125 |
| Chronic Lymphocytic Leukaemia | CD5, CD19 |
| Glioma | EGFR, Vimentin |
| Multiple myeloma | B cell maturation antigen (BCMA), CD138, transmembrane activator, calcium modulator, and cyclophilin ligand interactor (TACI) |
| Renal Cell Carcinoma | Carbonic anhydrase IX, G250 |
| Prostate cancer | PSMA |
| Bowel cancer | A33 |

Cell

The present invention also relates to a genetically modified cell, comprising a CAR or transgenic TCR, obtainable (or obtained) by the method of the invention.

A "starting population of cells" as used herein refers to a sample of cells which will be used to produce genetically modified cells which comprise a CAR or a transgenic TCR.

The starting population of cells may be obtained from any source of blood cells or peripheral blood mononuclear cells (PBMCs). The source cells may be provided fresh or may be cryopreserved prior to use. The starting population of cells may be used without any further manipulation or may be used after an isolation or enrichment step. Methods for isolating or enriching white blood cells are known in the art. For example, white blood cells or PBMCs may be obtained from whole blood by various methods e.g. density gradient separation, such as using Ficoll-Paque density gradient media; by magnetic bead separation, such as MACS Milteyni Biotec CD3, CD4 or CD8 beads; by elutriation or any other method. Separation or isolation of cells may be automated or may be performed manually.

The starting population of cells may be from blood e.g. from a peripheral blood sample or from a biopsy. The starting population of cells may be peripheral blood mononuclear cells. The starting population of cells may be a leukapheresate.

Suitably, the starting population of cells may be obtained from the subject ($1^{st}$ party). Suitably, the starting population of cells may be obtained from a donor ($2^{nd}$ party). Suitably, the starting population of cells may be obtained from a donor who is an unconnected donor ($3^{rd}$ party).

Alternatively, the cells may be derived from ex vivo differentiation of inducible progenitor cells or embryonic progenitor cells to, for example, T cells. Alternatively, an immortalized cell line which retains its lytic function and could act as a therapeutic may be used.

Suitably, the starting population may be whole blood obtained from the subject. Suitably, the starting population may be PBMCs obtained from the subject. Suitably, the starting population may be a leukapheresate obtained from the subject.

Suitably, the starting population may be whole blood obtained from a donor. Suitably, the starting population may be PBMCs obtained from a donor. Suitably, the starting population may be a leukapheresate obtained from a donor.

A "depleted starting population" as used herein refers to the population of cells which remains after cells which express the target antigen have been depleted from the starting population. In other words, the starting population has been depleted of cells which express the target antigen i.e. the depleted starting population is target antigen depleted.

"Depleted" as used herein means that cells of a specific type (e.g. cells which express a CAR or transgenic TCR target antigen) have been selectively reduced in number or have been eliminated from a population of cells.

"Transduced or transfected cells" as used herein refers to the cell population which has undergone the transduction or transfection process. This population of cells may contain a mixture of cells which have been successfully genetically modified and those which have not.

An "genetically modified cell" as used herein means a cell which has been modified to comprise or express a CAR or transgenic TCR. Methods for engineering cells are known in the art and include but are not limited to genetic modification of cells e.g. by transduction such as retroviral or lentiviral transduction, transfection (such as transient transfection—DNA or RNA based) including lipofection, polyethylene glycol, calcium phosphate and electroporation. Any suitable method may be used to introduce a nucleic acid sequence into a cell which encodes a CAR or transgenic TCR.

Suitably, a genetically modified cell is a cell whose genome has been modified e.g. by transduction or by transfection. Suitably, a genetically modified cell is a cell whose genome has been modified by retroviral transduction. Suitably, a genetically modified cell is a cell whose genome has been modified by lentiviral transduction.

As used herein, the term "introduced" refers to methods for inserting foreign DNA or RNA into a cell. As used herein the term introduced includes both transduction and transfection methods. Transfection is the process of introducing nucleic acids into a cell by non-viral methods. Transduction is the process of introducing foreign DNA or RNA into a cell via a viral vector.

Genetically modified cells according to the invention may be generated by introducing DNA or RNA coding for the CAR or transgenic TCR by one of many means including transduction with a viral vector, transfection with DNA or RNA.

Cells may be activated and/or expanded prior to the introduction of a nucleic acid sequence encoding a CAR or transgenic TCR, for example by treatment with an anti-CD3 monoclonal antibody or both anti-CD3 and anti-CD28 monoclonal antibodies.

Suitably, the genetically modified cell may be autologous.
Suitably, the cell may be allogeneic.
In one embodiment, the genetically modified cell may be a PBMC.
Suitably, the genetically modified cell may be a B cell.
Suitably the genetically modified cell may be an NK cell.
Suitably the genetically modified cell may be a T cell.
The genetically modified cell may be a cytolytic immune cell.

"Cytolytic immune cell" as used herein is a cell which directly kills other cells. Cytolytic cells may kill cancerous cells; virally infected cells or other damaged cells. Cytolytic immune cells include T cells and Natural killer (NK) cells.

Cytolytic immune cells can be T cells or T lymphocytes which are a type of lymphocyte that play a central role in cell-mediated immunity. T cells can be distinguished from other lymphocytes, such as B cells and NK cells, by the presence of a TCR on their cell surface. There are various types of T cell, as summarised below.

Helper T cells (TH cells) assist other white blood cells in immunologic processes, including maturation of B cells into plasma cells and memory B cells, and activation of cytotoxic T cells and macrophages. TH cells express CD4 on their surface. TH cells become activated when they are presented with peptide antigens by MHC class II molecules on the surface of antigen presenting cells (APCs). These cells can differentiate into one of several subtypes, including TH1, TH2, TH3, TH17, Th9, or TFH, which secrete different cytokines to facilitate different types of immune responses.

Cytolytic T cells (TC cells, or CTLs) destroy virally infected cells and tumour cells, and are also implicated in transplant rejection. CTLs express the CD8 at their surface. CTLs may be known as CD8+ T cells. These cells recognize their targets by binding to antigen associated with MHC class I, which is present on the surface of all nucleated cells. Through IL-10, adenosine and other molecules secreted by regulatory T cells, the CD8+ cells can be inactivated to an anergic state, which prevent autoimmune diseases such as experimental autoimmune encephalomyelitis.

Memory T cells are a subset of antigen-specific T cells that persist long-term after an infection has resolved. They quickly expand to large numbers of effector T cells upon re-exposure to their cognate antigen, thus providing the immune system with "memory" against past infections. Memory T cells comprise three subtypes: central memory T cells (TCM cells) and two types of effector memory T cells (TEM cells and TEMRA cells). Memory cells may be either CD4+ or CD8+. Memory T cells typically express the cell surface protein CD45RO.

Regulatory T cells (Treg cells), formerly known as suppressor T cells, are crucial for the maintenance of immunological tolerance. Their major role is to shut down T cell-mediated immunity toward the end of an immune reaction and to suppress auto-reactive T cells that escaped the process of negative selection in the thymus.

Two major classes of CD4+ Treg cells have been described—naturally occurring Treg cells and adaptive or induced Treg cells.

Naturally occurring Treg cells (also known as CD4+ CD25+FoxP3+ Treg cells) arise in the thymus and have been linked to interactions between developing T cells with both myeloid (CD11c+) and plasmacytoid (CD123+) dendritic cells that have been activated with TSLP. Naturally occurring Treg cells can be distinguished from other T cells by the presence of an intracellular molecule called FoxP3. Mutations of the FOXP3 gene can prevent regulatory T cell development, causing the fatal autoimmune disease IPEX.

As used herein, the term "natural T reg" means a thymus-derived Treg. Natural T regs are CD4+CD25+FOXP3+ Helios+ Neuropilin 1+. Compared with iTregs, nTregs have increased expression of PD-1 (programmed cell death-1, pdcd1), neuropilin 1 (Nrp1), Helios (Ikzf2), and CD73. nTregs may be distinguished from iTregs on the basis of the expression of Helios protein or Neuropilin 1 (Nrp1) individually.

Adaptive Treg cells (also known as Tr1 cells or Th3 cells) may originate during a normal immune response.

Peripherally generated Tregs may be referred to as induced Treg (iTreg) cells.

As used herein, the term "induced regulatory T cell" (iTreg) means a CD4+ CD25+ FOXP3+ Helios− Neuropilin 1− T cell which develops from mature CD4+ conventional T cells outside of the thymus. For example, iTregs can be induced in vitro from CD4+ CD25−FOXP3− cells in the presence of IL-2 and TGF-β.

Suitably the cell may be a T cell. Suitably the cell may be a helper T cell. Suitably the cell may be a cytolytic T cell. Suitably the cell may be a memory T cell. Suitably the cell may be a regulatory T cell (Treg). Suitably the cell may be a naturally occurring Treg or an adaptive Treg.

Natural Killer Cells (or NK cells) are a type of cytolytic cell which form part of the innate immune system. NK cells provide rapid responses to innate signals from virally infected cells in an MHC independent manner.

NK cells (belonging to the group of innate lymphoid cells) are defined as large granular lymphocytes (LGL) and constitute the third kind of cells differentiated from the common lymphoid progenitor generating B and T lymphocytes. NK cells are known to differentiate and mature in the bone marrow, lymph node, spleen, tonsils and thymus where they then enter into the circulation.

Suitably the cell may be a natural killer cell.
Suitably, the cell may be a stem cell.
In one embodiment, the cell may be a progenitor cell.
As used herein, the term "stem cell" means an undifferentiated cell which is capable of indefinitely giving rise to more stem cells of the same type, and from which other, specialised cells may arise by differentiation. Stem cells are multipotent. Stem cells may be for example, embryonic stem cells or adult stem cells.

As used herein, the term "progenitor cell" means a cell which is able to differentiate to form one or more types of cells but has limited self-renewal in vitro.

Suitably, the cell may be any cell capable of differentiating into a cytolytic immune cell.

Suitably, the cell may be capable of being differentiated into a T cell or NK cell.

Suitably, the cell may be an embryonic stem cell (ESC). Suitably, the cell may be a haematopoietic stem cell or haematopoietic progenitor cell. Suitably, the cell may be an induced pluripotent stem cell (iPSC). Suitably, the cell may be obtained from umbilical cord blood. Suitably, the cell may be obtained from adult peripheral blood.

In some aspects, hematopoietic stem and progenitor cell (HSPCs) may be obtained from umbilical cord blood. Cord blood can be harvested according to techniques known in the art (e.g., U.S. Pat. Nos. 7,147,626 and 7,131,958 which are incorporated herein by reference).

In one aspect, HSPCs may be obtained from pluripotent stem cell sources, e.g., induced pluripotent stem cells (iPSCs) and embryonic stem cells (ESCs).

As used herein, the term "hematopoietic stem and progenitor cell" or "HSPC" refers to a cell which expresses the antigenic marker CD34 (CD34+) and populations of such cells. In particular embodiments, the term "HSPC" refers to a cell identified by the presence of the antigenic marker CD34 (CD34+) and the absence of lineage (lin) markers. The population of cells comprising CD34+ and/or Lin(−) cells includes haematopoietic stem cells and hematopoietic progenitor cells.

HSPCs can be obtained or isolated from bone marrow of adults, which includes femurs, hip, ribs, sternum, and other bones. Bone marrow aspirates containing HSPCs can be obtained or isolated directly from the hip using a needle and syringe. Other sources of HSPCs include umbilical cord blood, placental blood, mobilized peripheral blood, Wharton's jelly, placenta, fetal blood, fetal liver, or fetal spleen. In particular embodiments, harvesting a sufficient quantity of HSPCs for use in therapeutic applications may require mobilizing the stem and progenitor cells in the subject.

As used herein, the term "induced pluripotent stem cell" or "iPSC" refers to a non-pluripotent cell that has been reprogrammed to a pluripotent state. Once the cells of a subject have been reprogrammed to a pluripotent state, the cells can then be programmed to a desired cell type, such as a hematopoietic stem or progenitor cell (HSC and HPC respectively).

As used herein, the term "reprogramming" refers to a method of increasing the potency of a cell to a less differentiated state.

As used herein, the term "programming" refers to a method of decreasing the potency of a cell or differentiating the cell to a more differentiated state.

The cells of the invention may be any of the cell types mentioned above.

A "population of genetically modified cells" as used herein means one or more genetically modified cells according to the present invention.

Suitably a population of genetically modified cells as used herein may mean two or more (or a plurality of) genetically modified cells according to the present invention.

A genetically modified cell or population of genetically modified cells of the present invention may be made by:
 (i) providing a starting population of cells;
 (ii) depleting said starting population of cells which express a target antigen; and
 (iii) introducing into a cell in the depleted starting population a nucleic acid sequence which encodes a CAR or transgenic TCR against the target antigen.

In one embodiment, the cell or population of cells may be activated before the CAR or transgenic TCR is introduced into the cell (iii).

In another embodiment, the cell or population of cells may not be activated before the CAR or transgenic TCR is introduced into the cell (iii).

In one embodiment (iii) introducing into a cell in the depleted starting population a nucleic acid sequence which encodes a CAR or transgenic TCR against the target antigen is performed sequentially with (ii) depleting said starting population of cells which express a target antigen.

In one embodiment (iii) introducing into a cell in the depleted starting population a nucleic acid sequence which encodes a CAR or transgenic TCR against the target antigen is performed after (ii) depleting said starting population of cells which express a target antigen.

Optionally, the method may comprise performing (iii) (introducing into a cell in the depleted starting population a nucleic acid sequence which encodes a CAR or transgenic TCR against the target antigen) before (ii) (depleting said starting population of cells which express a target antigen), i.e. the nucleic acid sequence which encodes a CAR or transgenic TCR against the target antigen may be introduced into a cell before the cells are depleted of cells which express a target antigen.

Optionally, the method may additionally comprise isolating a cell containing sample from a subject. This cell containing sample may be used as the staring population of cells.

Optionally, the cells for use in the present invention may be activated and/or expanded prior to the introduction of a nucleic acid sequence which encodes a CAR or transgenic TCR.

Any method known in the art for activating and/or expanding cells may be used in the method of the invention. For example cells for use in the present invention e.g. T cells may be activated and/or expanded by treatment with an anti-CD3 monoclonal antibody or both anti-CD3 and anti-CD28 monoclonal antibodies.

Suitably, interleukin 7 (IL-7) and/or interleukin 15 (IL-15) may be used to expand cells e.g. T cells in vitro. Suitably, interleukin 2 (IL-2) may be used for the expansion of cells in vitro.

NK cells for use in the present invention may be activated and/or expanded by treatment with cytokines such as interleukin 2 (IL-2) and/or interleukin 15 (IL-15). Incubation with accessory cells such as monocytes, B-lymphoblastoid cells or cell lines which express stimulatory molecules may be used to provide additional signals for expansion of NK cells.

As used herein "activated" means that a cell has been stimulated, causing the cell to proliferate, differentiate or initiate an effector function.

Methods for measuring cell activation are known in the art and include, for example, measuring the expression of activation markers by flow cytometry, such as the expression of CD69, CD25, CD38 or HLA-DR or measuring intracellular cytokines.

As used herein "expanded" means that a cell or population of cells has been induced to proliferate.

The expansion of a population of cells may be measured for example by counting the number of cells present in a population. The phenotype of the cells may be determined by methods known in the art such as flow cytometry.

In one aspect, the method according to the present invention produces a population of engineered cells (e.g. genetically modified cells) which comprise a chimeric antigen receptor or a transgenic T-cell receptor.

Suitably a genetically modified cell or population of genetically modified cells according to the present invention may be made by the method according to the invention.

In one aspect, the population of genetically modified cells according to the present invention or obtainable (e.g. obtained) by a method according to the present invention are less differentiated than genetically modified cells which were not prepared according to a method of the invention i.e. were prepared without depleting cells which express the target antigen of the CAR or transgenic TCR.

As used herein "differentiated" refers to the stage of development of a particular cell within the linear progression of differentiation of that cell type. For example, CD4+ and CD8+ T cells can be categorized into distinct memory subsets based on their differentiation states. CD4+ and CD8+ T cells follow a progressive pathway of differentiation from naïve T cells into central memory and effector memory cell populations. The differentiation state of CD8+ T cells is inversely related to their capacity to proliferate and persist.

Preclinical studies suggest that improved antitumor responses are achieved when genetically modified T cells are in the early stages of differentiation (such as naïve or central memory cells). Central memory cells have improved in vivo persistence compared with effector memory cells.

In one aspect, the population of genetically modified cells according to the invention or obtainable by a method according to the invention are more naïve than genetically modified cells which were not prepared according to a method of the invention i.e. were prepared without depleting cells which express the target antigen of the CAR or transgenic TCR.

As used herein, "naïve" means a cell which is not fully differentiated. A naïve T cell may not have encountered antigen.

Naïve T cells may be characterised by the surface expression of L selection (CD62L), the absence of activation markers CD25, CD44 or CD69 and the absence of memory CD45RO isoform e.g. naïve T cells may be $CD62L^{Hi}CD25^{Lo}CD44^{Lo}CD69^{Lo}$. Naïve T cells also express functional IL-7 receptors, consisting of subunits IL-7 receptor-α, CD127, and common-γ chain, CD132.

In one aspect, a naïve cell subset may be defined as CCR7+/CD45RA+ cells. Suitably, a naive cell subset may be further defined as CCR7+/CD45RA+/CD62L+/CD27+ cells.

Suitably, the genetically modified cells according to the present invention or obtainable (e.g. obtained) by a method according to the present invention may have increased expression of CD27 and/or CD62L compared with genetically modified cells which were not prepared according to a method of the present invention i.e. were prepared without depleting cells which express the target antigen of the CAR or transgenic TCR.

Without wishing to be bound by theory, a more naïve or immature genetically modified cell population is advantageous for use in therapy because naïve cells exhibit enhanced persistence in vivo and enhanced cytolytic activity when compared to cells with a more differentiated phenotype.

Suitably, the method according to the present invention may produce more naïve or central memory cells than a method which does not deplete cells which express the target antigen of the CAR or transgenic TCR. Suitably, at least 75% of the genetically modified cells may be naïve or central memory cells. Suitably, at least 80% of the genetically modified cells may be naïve or central memory cells. Suitably, at least 85% of the genetically modified cells may be naïve or central memory cells.

Suitably, the method according to the present invention may produce fewer effector and effector memory cells than a method which does not deplete cells which express the target antigen of the CAR or transgenic TCR. Suitably, fewer than 25% of the genetically modified cells may be effector or effector memory cells. Suitably, fewer than 20% of the genetically modified cells may be effector or effector memory cells. Suitably, fewer than 15% of the genetically modified cells may be effector or effector memory cells.

In one aspect, the population of genetically modified cells according to the present invention or obtainable (or obtained) by a method according to the present invention are less exhausted compared with genetically modified cells which were not prepared according to a method of the invention i.e. prepared without depleting cells which express the target antigen of the CAR or transgenic TCR.

As used herein "exhaustion" or "exhausted" means that the cell exhibits decreased effector functions and/or altered phenotype. Immune cell exhaustion describes the status of dysfunction of immune cells, usually under the setting of tumours or chronic infection. Exhaustion may be accompanied by phenotypic changes, epigenetic modifications and alterations in transcriptional profiles.

Effector functions may include the production of effector cytokines and direct cytotoxic activity.

Suitably the population of genetically modified cells according to the present invention or obtainable (or obtained) by a method according to the present invention may have decreased expression of one or more exhaustion markers compared with genetically modified cells which were not prepared according to a method of the present invention i.e. were prepared without depleting cells which express the target antigen of the CAR or transgenic TCR.

Suitably, one or more exhaustion markers may be two exhaustion markers. Suitably, one or more exhaustion markers may be three exhaustion markers. Suitably, one or more exhaustion markers may be four exhaustion markers. Suitably, one or more exhaustion markers may be five exhaustion markers. Suitably, one or more exhaustion markers may be six exhaustion markers. Suitably, one or more exhaustion markers may be seven exhaustion markers.

For example, in the context of NK cells, effector functions may include production of interferon gamma (IFN-γ). Other effector functions of NK cells include direct cytotoxic activity, such as activity dependent on perforin and granzyme, or induction of target cell apoptosis by tumour necrosis factor alpha (TNF-α), Fas ligand (FasL) and TNF-related apoptosis-inducing ligand (TRAIL).

Suitably, exhausted NK cells may produce decreased amounts of effector cytokines e.g. IFN-γ, compared with non-exhausted NK cells. Suitably, exhausted NK cells may have decreased cytolytic activity and may, for example, produce decreased amounts of CD107a and/or granzyme B and/or perforin compared with non-exhausted NK cells.

Suitably the one or more exhaustion markers may be selected from the group consisting of: IFN-γ, TNF-α, FasL, TRAIL, CD107a, granzyme B and perforin. Suitably the one or more exhaustion markers may be selected from the group consisting of: IFN-γ, TNF-α, FasL, TRAIL, CD107a, granzyme B and perforin wherein the genetically modified cell is an NK cell.

Suitably, the one or more exhaustion markers may comprise decreased IFN-γ production. Suitably, the one or more exhaustion markers may comprise decreased TNF-α production. Suitably, the one or more exhaustion markers may comprise decreased expression of FASL. Suitably, the one or more exhaustion markers may comprise decreased expression of TRAIL. Suitably, the one or more exhaustion markers may comprise decreased expression of CD107a. Suitably, the one or more exhaustion markers may comprise decreased production of granzyme B. Suitably, the one or more exhaustion markers may comprise decreased production of perforin.

For example, in the context of T cells, exhaustion may be defined by poor effector function, sustained expression of inhibitory receptors and/or a transcriptional state distinct from that of functional effector or memory T cells. For example, exhausted T cells may express high levels of PD1, Tim3, Lag3, CD43 (1611), CD69 and inhibitory receptors but low levels of CD62L and CD127 and decreased interleukin-2 (IL-2), TNF-α and IFN-γ production.

Suitably, the one or more exhaustion markers may comprise increased (e.g. high) expression of PD1. Suitably, the one or more exhaustion markers may comprise increased (e.g. high) expression of Tim3. Suitably, the one or more exhaustion markers may comprise increased (e.g. high) expression of Lag3. Suitably, the one or more exhaustion markers may comprise increased (e.g. high) expression of CD43 (1B11). Suitably, the one or more exhaustion markers may comprise increased (e.g. high) expression of CD69. Suitably, the one or more exhaustion markers may comprise increased (e.g. high) expression of inhibitory receptors. Suitably, the one or more exhaustion markers may comprise decreased (e.g. low) expression of CD62L. Suitably, the one or more exhaustion markers may comprise decreased (e.g. low) expression of CD127. Suitably, the one or more exhaustion markers may comprise decreased (e.g. low) IL-2 production upon target encounter. Suitably, the one or more exhaustion markers may comprise decreased (e.g. low) TNF-α production upon target encounter. Suitably, the one or more exhaustion markers may comprise decreased (e.g. low) IFN-γ production upon target encounter.

Suitably, the one or more exhaustion markers may be selected from the group consisting of: PD1, Lag3 and Tim3. Suitably, the one or more exhaustion markers may comprise PD1. Suitably, the one or more exhaustion markers may comprise Lag3. Suitably, the one or more exhaustion markers may comprise Tim3. Suitably, the one or more exhaustion markers may be selected from the group consisting of: PD1, Lag3 and Tim3 wherein the genetically modified cell is a T cell.

The inclusion of a depletion step in the method according to the present invention advantageously significantly reduces or abolishes cytokine production during the manufacturing process compared to an equivalent manufacturing process which does not contain a target antigen expressing cell depletion step.

Figure 8:
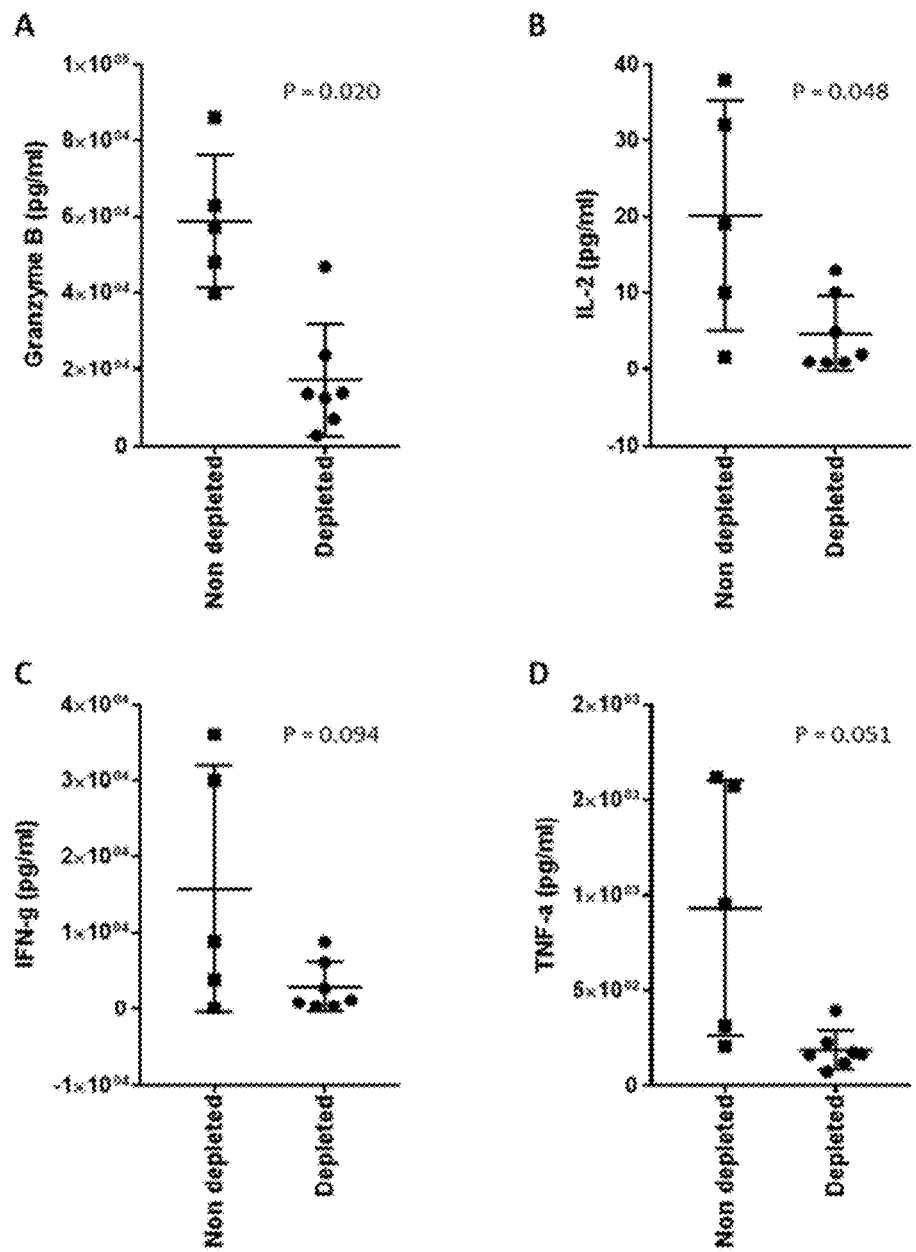
FIG. 8—Graphs showing results of cytokine release assay. End of process data to show concentrations of (A) granzyme B, (B) IL-2, (C) IFN-g and (D) TNF-a released into the culture (non depleted n=5; depleted n=7; 5 matched pairs. Paired t-tests n=5).

Cytokine analysis on the media from the final cultures (i.e. at day 6-10 post activation) during CAR-T cell production demonstrated consistently low levels of IL-2, TNFα, IFNγ and Granzyme B production by target antigen depleted cells, but proved highly variable with non-depleted cells and, on average, significantly higher for Granzyme B and IL-2 (FIG. 8).

Figure 9:
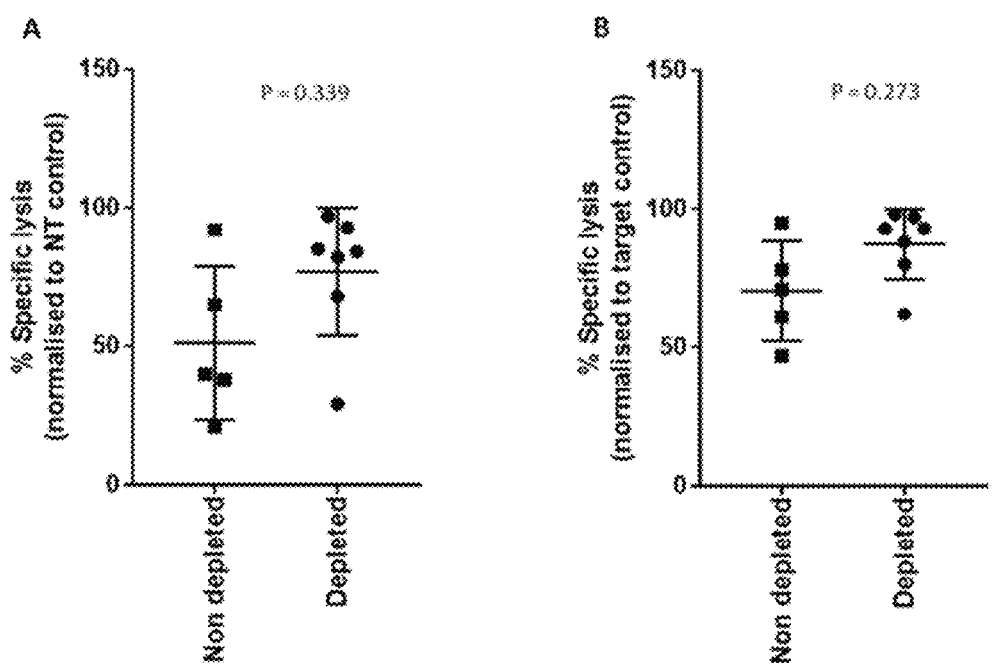
FIG. 9—Graphs showing results of cytotoxicity assay: target cell killing. Data to show the percentage of TRBC1+ Raji cells killed after 48 h (A) relative to non-transduced control cells (normalised for non-specific killing), (B) relative to TRBC1+ Raji cells cultured alone (normalised for ordinary cell death) (non-depleted n=5; depleted n=7).
Figure 10:
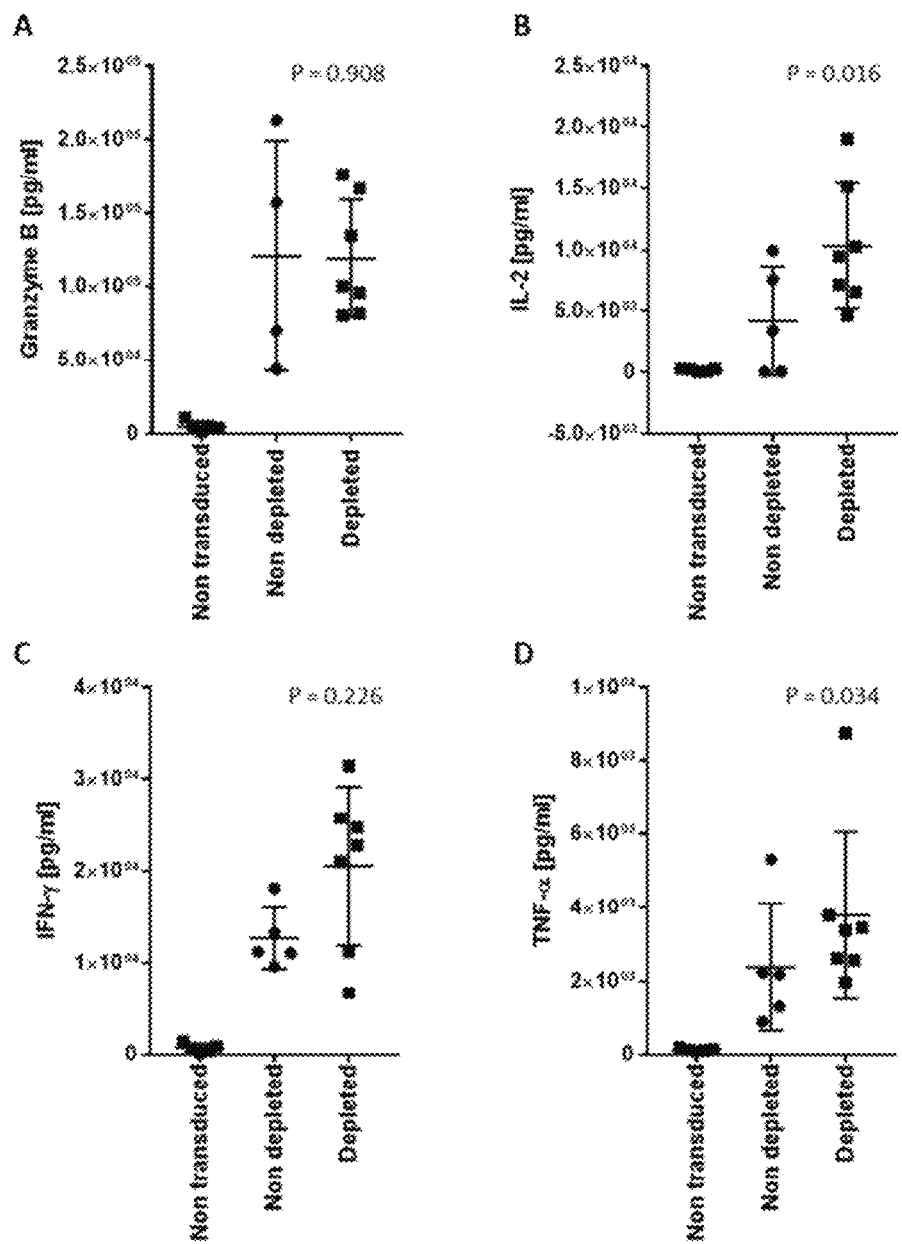
FIG. 10—Graphs showing results of the cytotoxicity: cytokine release assay. Data showing concentrations of (A) granzyme B, (B) IL-2, (C) IFN-g and (D) TNF-a released after 48 h (non depleted n=5; depleted n=7; 5 matched pairs. Paired t-test n=5).

Cells according to the present invention or obtainable (e.g. obtained) by a method according to the present invention, when used in a cytotoxicity functional assay, show significantly increased cytokine production of IFN-γ, IL-2 and TNF-α following co-culture with target cells (i.e. cells expressing target antigen) compared with cells produced by an equivalent manufacturing process which does not contain a target antigen depletion step (FIG. 9 and FIG. 10).

In one aspect, more than 10%, more than 15%, more than 20%, more than 25%, more than 30%, or more than 35% of the population of genetically modified cells according to the present invention or obtainable (or obtained) by a method according to the present invention may be naïve (CCCR7+/CD45RA+) and CD62L+/CD27+. Suitably more than 10% of the genetically modified cells according to the invention may be naïve (CCCR7+/CD45RA+) and CD62L+/CD27+. Suitably more than 15% of the genetically modified cells according to the invention may be naïve (CCCR7+/CD45RA+) and CD62L+/CD27+. Suitably more than 20% of the genetically modified cells according to the invention may be naïve (CCCR7+/CD45RA+) and CD62L+/CD27+. Suitably more than 30% of the genetically modified cells according to the invention may be naïve (CCCR7+/CD45RA+) and CD62L+/CD27+. Suitably more than 40% of the genetically modified cells according to the invention may be naïve (CCCR7+/CD45RA+) and CD62L+/CD27+.

Suitably, the proportion of naïve cells may be measured in the CD8+ T cell subset.

In one aspect, fewer than 30%, fewer than 25%, fewer than 20%, fewer than 15%, fewer than 10%, fewer than 5% of the population of genetically modified cells according to the present invention or obtainable (or obtained) by a method according to the present invention may express multiple exhaustion markers. Suitably fewer than 30% of the genetically modified cells according to the invention may exhibit multiple exhaustion markers. Suitably fewer than 25% of the genetically modified cells according to the invention may exhibit multiple exhaustion markers. Suitably fewer than 20% of the genetically modified cells according to the invention may exhibit multiple exhaustion markers. Suitably fewer than 15% of the genetically modified cells according to the invention may exhibit multiple exhaustion markers.

Suitably the multiple exhaustion markers may be selected from increased expression (e.g. high levels) of PD1, Tim3, Lag3, CD43 (1B11), CD69 and inhibitory receptors and decreased expression of (e.g. low levels) of CD62L and CD127 and decreased (e.g. low) interleukin-2 (IL-2), TNF-α and IFN-γ production. Suitably the multiple exhaustion markers may be selected from increased expression of (e.g. high levels) of Lag3, PD1 and Tim3.

In one aspect, the population of genetically modified cells according to the present invention or obtainable (or obtained) by a method according to the present invention have increased levels of CAR or transgenic TCR transduction efficiency compared with genetically modified cells which were not prepared according to a method of the present invention i.e. were prepared without depleting cells which express the target antigen of the CAR or transgenic TCR.

Suitably, the level of transduction efficiency in the population of genetically modified cells according to the present invention or obtainable (or obtained) by a method according to the present invention may be at least 10%, 20%, 30%, 40%, 50%, 60%, 70%, 80%, 90% higher than transduction efficiency of genetically modified cells which were not prepared according to a method of the present invention i.e. were prepared without depleting cells which express the target antigen of the CAR or transgenic TCR.

Suitably, the level of transduction efficiency in the population of genetically modified cells according to the present invention or obtainable (or obtained) by a method according to the present invention may be at least 50% higher than transduction efficiency of genetically modified cells which were not prepared according to a method of the present invention i.e. were prepared without depleting cells which express the target antigen of the CAR or transgenic TCR. Suitably, the level of transduction efficiency in the population of genetically modified cells according to the present invention or obtainable (or obtained) by a method according to the present invention may be at least 60% higher than transduction efficiency of genetically modified cells which were not prepared according to a method of the present invention i.e. were prepared without depleting cells which express the target antigen of the CAR or transgenic TCR. Suitably, the level of transduction efficiency in the population of genetically modified cells according to the present invention or obtainable (or obtained) by a method according to the present invention may be at least 70% higher than transduction efficiency of genetically modified cells which were not prepared according to a method of the present invention i.e. were prepared without depleting cells which express the target antigen of the CAR or transgenic TCR. Suitably, the level of transduction efficiency in the population of genetically modified cells according to the present invention or obtainable (or obtained) by a method according to the present invention may be at least 80% higher than transduction efficiency of genetically modified cells which were not prepared according to a method of the present invention i.e. were prepared without depleting cells which express the target antigen of the CAR or transgenic TCR. Suitably, the level of transduction efficiency in the population of genetically modified cells according to the present invention or obtainable (or obtained) by a method according to the present invention may be at least 90% higher than transduction efficiency of genetically modified cells which were not prepared according to a method of the present invention i.e. were prepared without depleting cells which express the target antigen of the CAR or transgenic TCR.

In one aspect, at least 5%, at least 10%, at least 15%, at least 20%, at least 25%, at least 30%, at least 40%, at least 50% or at least 60% of the population of the transduced or transfected cells comprise a CAR or transgenic TCR. Suitably at least 40% of the population of transduced or transfected cells comprises a CAR or transgenic TCR. Suitably at least 50% of the population of the transduced or transfected cells comprise a CAR or transgenic TCR. Suitably at least 60% of the population of transduced or transfected cells comprises a CAR or transgenic TCR.

Suitably, the percentage of cells which express target antigen and which have been transduced or transfected to express a CAR or transgenic CAR is less than 5%. Suitably, the percentage of cells which express target antigen and which have been transduced or transfected to express a CAR or transgenic CAR is less than 3%. Suitably, the percentage of cells which express target antigen and which have been transduced or transfected to express a CAR or transgenic CAR is less than 2%. Suitably, the percentage of cells which express target antigen and which have been transduced or transfected to express a CAR or transgenic CAR is less than 1%. Suitably, the percentage of cells which express target antigen and which have been transduced or transfected to express a CAR or transgenic CAR is undetectable.

Method

There is provided a method of preparing a population of genetically modified cells which comprise a chimeric antigen receptor (CAR) or a transgenic T-cell receptor (TCR).

Methods of preparing a population of genetically modified cells for cellular therapy are known generally in the art. Methods of preparing genetically modified cells for cellular therapy may include some or all of the following steps:

The starting material may initially be frozen e.g. the starting population of cells may be frozen once it is obtained from the donor e.g. source of cells. If frozen material is used then thawing and an optional rest period may occur before proceeding to the next step. Alternatively, fresh starting material may be used. The starting material may undergo initial purification/enrichment for white cells (e.g. Ficoll gradient) of for T cells.

The starting material may then be activated e.g. the T cells may be activated. This may be performed by any methods known in the art e.g. using soluble CD3/CD28 antibodies, or CD3/CD28 beads (e.g. Dynabeads), or CD3/28 nanomatrix (e.g TransAct). As is understood in the art, the length of the activation step may be varied e.g. from under an hour to beyond 72 hours before proceeding to the next step.

The activated cells may then be transduced with the viral vector (e.g. retroviral or lentiviral). This may be done in the presence of a transduction enhancer (e.g. retronectin, or polybrene), or by spinoculation or by simple incubation. Non viral vectors may also be used for the genetic modification step (e.g. using RNA electroporation or transposition using DNA).

The cells may then undergo an expansion step that may last from hours to several days, depending on the final dose of cells required. Generally the more cells required, the longer the expansion step.

The cells at the end of the manufacturing process may be used fresh, or preferably may be frozen before use.

The overall process may therefore take from 2 to 18 days. Typically the overall process takes 6-10 days.

During the process the cells may be cultured in cell growth medium that may contain additional supplements. Such supplements may be human serum, fetal bovine serum, human serum albumin and/or cytokines (such as IL2, IL7 and/or IL15, IL21).

There is provided a method of preparing a population of genetically modified cells which comprise a chimeric antigen receptor (CAR) or a transgenic T-cell receptor (TCR) comprising:

(i) providing a starting population of cells;
(ii) depleting said starting population of cells which express a target antigen; and
(iii) introducing into a cell in the depleted starting population a nucleic acid sequence which encodes a CAR or transgenic TCR against the target antigen.

In one embodiment (iii) introducing into a cell in the depleted starting population a nucleic acid sequence which encodes a CAR or transgenic TCR against the target antigen is performed sequentially with (ii) depleting said starting population of cells which express a target antigen.

In one embodiment (iii) introducing into a cell in the depleted starting population a nucleic acid sequence which encodes a CAR or transgenic TCR against the target antigen is performed after (ii) depleting said starting population of cells which express a target antigen.

Optionally, the method may comprise performing (iii) (introducing into a cell in the depleted starting population a nucleic acid sequence which encodes a CAR or transgenic TCR against the target antigen) before (ii) (depleting said starting population of cells which express a target antigen), i.e. the nucleic acid sequence which encodes a CAR or transgenic TCR against the target antigen may be introduced into a cell before the cells are depleted of cells which express a target antigen.

"MOI"/"multiplicity of infection" as used herein indicates the number of infectious vector particles per cell used in transduction. For example, a MOI of 1 means the addition of $10^4$ infectious vector particles to $10^4$ cells. The number of infectious particles is obtained by titration of the viral vector on a permissive cell line.

Suitably, the transduced cell type may be the same cell type that has been used for the titration. In this case, a MOI of 1 should result in a mean number of vector integrations per cell of 1 as estimated by quantitative PCR or other suitable method.

Suitably, the depleted starting population may be transduced with low multiplicity of infection (MOI). For example, a lower MOI may be used in methods of the invention to achieve a particular level of cell transduction compared with the MOI required to transduce cells prepared by methods which do not deplete target antigen positive cells.

Advantageously, transducing a population of cells with a lower MOI may prevent the transduction of cells which express the target antigen whilst allowing transduction of cells which do not express the target antigen.

Suitably, the MOI is selected such that cells which do not express the target antigen are transduced and cells which express the target antigen are not transduced.

Suitably, the MOI is selected such that cells which do not express the target antigen are transduced to a greater extent than cells which express the target antigen. The population of genetically modified cells may have a higher ratio of cells which do not express the target antigen:cells which express the target antigen that the cells prior to transduction.

Suitably, the MOI is selected such that at least 5% of cells which do not express the target antigen are transduced and cells which express the target antigen are not transduced.

Suitably, the MOI is selected such that at least 10% of cells which do not express the target antigen are transduced and cells which express the target antigen are not transduced. Suitably, the MOI is selected such that at least 15% of cells which do not express the target antigen are transduced and cells which express the target antigen are not transduced.

Suitably, the MOI is selected such that at least 20% of cells which do not express the target antigen are transduced and cells which express the target antigen are not transduced.

Cells which express the target antigen may be "not transduced" in that such cells are undetectable, or transduced at minimal or very low levels, such as 1% or less.

Suitably, the method of the present invention advantageously may enable the use of a low MOI for transduction. Suitably, the MOI required to achieve 20-30% transduction of target antigen negative cells may be lower in the method of the invention, than in a corresponding method which does not deplete target antigen positive cells.

Without wishing to be bound by theory, the method of the present invention may provide a safety benefit for the manufacture of genetically modified cells because a lower MOI is required for transduction. Advantageously, cells which express the target antigen may not be transduced or transduced at minimal/very low levels by the method of the present invention.

As is known in the art, the use of transduction enhancers may alter the MOI required for transduction e.g. may lower the MOI required for transduction. Transduction enhancers are known in the art, such as VectoFusin or RetroNectin.

Suitably, the MOI may be chosen to achieve about 10-50% transduction. Suitably, the MOI may be chosen to achieve about 15-40% transduction. Suitably, the MOI may be chosen to achieve about 20-30% transduction.

Suitably, the MOI may be about 0.05, 0.1, 0.2, 0.3, 0.4, 0.5, 0.6, 0.7, 0.8, 0.9, 1, 1.1 or about 1.2. Suitably, the MOI range may be about 0.1-1.2. Suitably, the MOI range may be about 0.2-1.0. Suitably, the MOI range may be about 0.3-0.8. Suitably, the MOI range may be about 0.4-0.6.

Suitably, the MOI to achieve about 20-30% transduction may be about 0.05, 0.1, 0.2, 0.3, 0.4, 0.5, 0.6, 0.7, 0.8, 0.9, 1, 1.1 or about 1.2. Suitably, the MOI range to achieve about 20-30% transduction may be about 0.1-1.2. Suitably, the MOI range to achieve about 20-30% transduction may be about 0.2-1.0. Suitably, the MOI range to achieve about 20-30% transduction may be about 0.3-0.8. Suitably, the MOI range to achieve about 20-30% transduction may be about 0.4-0.6.

Suitably, the percentage of CAR or transgenic TCR target antigen positive cells may be lower in the depleted starting population or population of genetically modified cells than in the starting population.

Suitably the percentage of target antigen positive cells may be reduced by at least 10%, 20%, 30%, 40%, 50%, 60%, 70%, 80%, 90%, 95%, 98%, 99% or 100% in the depleted starting population or the population of genetically modified cells when compared with the percentage of target antigen positive cells in the starting population. Suitably, the percentage of target antigen positive cells may be reduced by at least 90%. Suitably, the percentage of target antigen positive cells may be reduced by at least 95%. Suitably, the percentage of antigen positive cells may be reduced by at least 98%. Suitably, the percentage of antigen positive cells may be reduced by at least 99% in the depleted starting population or in the population of genetically modified cells when compared with the percentage of target antigen positive cells in the starting population.

Suitably fewer than 40%, fewer than 30%, fewer than 20%, fewer than 10%, fewer than 9%, fewer than 8%, fewer than 7%, fewer than 6%, fewer than 5%, fewer than 4%, fewer than 3%, fewer than 2%, less than 1% of the depleted starting population may express the target antigen of the CAR or transgenic TCR.

Suitably fewer than 10% of the depleted starting population may express the target antigen of the CAR or transgenic TCR.

Suitably fewer than 5% of the depleted starting population may express the target antigen of the CAR or transgenic TCR.

Suitably fewer than 3% of the depleted starting population may express the target antigen of the CAR or transgenic TCR.

Suitably fewer than 2% of the depleted starting population may express the target antigen of the CAR or transgenic TCR.

Suitably less than 1% of the depleted starting population may express the target antigen of the CAR or transgenic TCR.

Suitably fewer than 10%, fewer than 9%, fewer than 8%, fewer than 7%, fewer than 6%, fewer than 5%, fewer than 4%, fewer than 3%, fewer than 2%, less than 1% of the genetically modified cells may express the target antigen of the CAR or transgenic TCR.

Suitably, fewer than 10% of the genetically modified cells may express the target antigen of the CAR or transgenic TCR.

Suitably, fewer than 5% of the genetically modified cells may express the target antigen of the CAR or transgenic TCR.

Suitably, less than 1% of the genetically modified cells may express the target antigen of the CAR or transgenic TCR.

Pharmaceutical Composition

The present invention also relates to a pharmaceutical composition comprising a genetically modified cell of the invention or a population of genetically modified cells according to the invention.

In one aspect, there is provided a pharmaceutical composition which comprises a population of genetically modified cells according to the present invention or obtainable by a method according to the present invention.

Suitably, the pharmaceutical composition may comprise cryopreserved genetically modified cells according to the present invention or obtainable by a method according to the present invention.

The pharmaceutical composition may additionally comprise a pharmaceutically acceptable carrier, diluent or excipient. The pharmaceutical composition may optionally comprise one or more further pharmaceutically active polypeptides and/or compounds. Such a formulation may, for example, be in a form suitable for intravenous infusion.

In one aspect, the present invention provides a method of reducing the number of cells in a pharmaceutical composition which express a target antigen and express a CAR or transgenic TCR against the target antigen comprising:
providing a starting population of cells;
depleting said starting population of cells which express a target antigen;
introducing into a cell in the depleted starting population a nucleic acid which encodes a CAR or transgenic TCR against the target antigen; and
incorporating the cells into a pharmaceutical composition.

Suitably, the number of cells which express a target antigen and express a CAR or transgenic TCR against the target antigen is reduced compared with a pharmaceutical composition produced without depleting the starting population of cells which express a target antigen.

In one aspect, the present invention provides a method of preparing a pharmaceutical composition comprising:
providing a starting population of cells;
depleting said starting population of cells which express a target antigen;
introducing into a cell in the depleted starting population a nucleic acid which encodes a CAR or transgenic TCR against the target antigen; and
incorporating the cells into a pharmaceutical composition.

Suitably, the cells may be expanded prior to incorporation into a pharmaceutical composition. For example, the cells may be expanded after the introduction of the nucleic acid which encodes the CAR or transgenic TCR against the target antigen.

Suitably, the cells may be activated prior to the introduction of a nucleic acid which encodes a CAR or transgenic TCR. For example, the cells may be activated before the introduction of the nucleic acid which encodes the CAR or transgenic TCR against the target antigen.

The cells may be activated and/or expanded by any method known in the art, for example by treatment with an anti-CD3 monoclonal antibody or both anti-CD3 and anti-CD28 monoclonal antibodies.

Suitably, the starting population of cells may previously have been frozen. If frozen cells are used, then the cells may be thawed and optionally, may be allowed to recover in culture before being processed.

The method may additionally comprise a step of enriching the starting population for white blood cells. Any methods for isolating or enriching white blood cells known in the art may be used. For example, white blood cells or PBMCs may be obtained from whole blood by various methods e.g. density gradient separation, such as using Ficoll-Paque density gradient media; by magnetic bead separation, such as MACS Milteyni Biotec CD3, CD4 or CD8 beads; by elutriation or any other method. Separation or isolation of cells may be automated or may be performed manually.

Suitably, the CAR or transgenic TCR may be introduced into the cell by transduction or transfection. Suitably, the CAR or transgenic TCR may be introduced into the cell by transduction and the multiplicity of infection may be chosen to be sufficient to transduce cells which do not express the target antigen and insufficient to transduce cells which express the target antigen.

Successful transduction or transfection of a cell with a nucleic acid encoding a CAR or transgenic TCR may be identified by methods known in the art, for example by flow cytometry.

Suitably, the method according to the present invention reduces the number of genetically modified cells which express the target antigen of the CAR or transgenic TCR i.e. the method reduces the number of genetically modified target cells in the pharmaceutical composition.

Suitably, the percentage of CAR or transgenic TCR target antigen positive cells may be lower in the pharmaceutical composition than in the starting population of cells. Suitably, less than 10% of the cells in the pharmaceutical composition may express the target antigen of the CAR or transgenic TCR. Suitably, less than 5% of the cells in the pharmaceutical composition may express the target antigen of the CAR or transgenic TCR. Suitably, less than 1% of the cells in the pharmaceutical composition may express the target antigen of the CAR or transgenic TCR.

Suitably, less than 10% of the cells in the pharmaceutical composition may express the CAR or transgenic TCR and the target antigen of the CAR or transgenic TCR. Suitably, less than 5% of the cells in the pharmaceutical composition may express the CAR or transgenic TCR and the target antigen of the CAR or transgenic TCR. Suitably, less than 1% of the cells in the pharmaceutical composition may express the CAR or transgenic TCR and the target antigen of the CAR or transgenic TCR.

In one aspect, the population of genetically modified cells according to the present invention is the active ingredient of the pharmaceutical composition.

As will be understood by those skilled in the art, a pharmaceutical composition may additionally comprise impurities. In the context of the present invention, an impurity may be a cell which expresses the target antigen. Suitably, in the context of the present invention, an impurity may be a cell which expresses the target antigen and which expresses the CAR or transgenic TCR. In the context of the present invention, an impurity may be a cell which does not express the CAR or transgenic TCR.

The present invention provides a method for reducing impurities (e.g. cells which express a target antigen of the CAR or transgenic TCR) in a pharmaceutical composition.

Suitably, a pharmaceutical composition according to the present invention comprises a population of cells wherein less than 10% of the cells are impurities. Suitably, a pharmaceutical composition according to the present invention comprises a population of cells wherein less than 5% of the cells are impurities. Suitably, a pharmaceutical composition according to the present invention comprises a population of cells wherein less than 3% of the cells are impurities. Suitably, a pharmaceutical composition according to the present invention comprises a population of cells wherein less than 2% of the cells are impurities. Suitably, a pharmaceutical composition according to the present invention comprises a population of cells wherein less than 1% of the cells are impurities.

Method of Treatment

The genetically modified cells of the present invention may be capable of killing target cells, such as cancer cells, virally infected cells or other damaged cells.

The genetically modified cells of the present invention may be used in therapy. The genetically modified cells of the present invention may be used for the treatment and/or prevention of disease. Suitably, a pharmaceutical composition comprising genetically modified cells according to the present invention may be used in therapy. Suitably, a pharmaceutical composition comprising genetically modified cells according to the present invention may be used for the treatment and/or prevention of disease.

It will be understood that the target antigen of the CAR or transgenic TCR will be chosen based on the required therapy. For example, if the CAR or transgenic TCR is for treating cancer, the target antigen of the CAR or transgenic TCR may be an antigen associated with cancer.

The genetically modified cells of the present invention may be used for the treatment of an infection, such as a viral infection.

The genetically modified cells of the invention may also be used for the control of pathogenic immune responses, for example in autoimmune diseases, allergies and graft-vs-host rejection.

The present invention provides a method for treating and/or preventing a disease which comprises the step of administering an genetically modified cell of the present invention to a subject.

The present invention provides a method for treating and/or preventing a disease which comprises the step of administering a pharmaceutical composition of the present invention to a subject.

The present invention also provides an genetically modified cell of the present invention for use in treating and/or preventing a disease.

The present invention also provides a pharmaceutical composition of the present invention for use in treating and/or preventing a disease.

The invention also relates to the use of an genetically modified cell according to the present invention in the manufacture of a medicament for treating and/or preventing a disease.

Suitably, the present methods of treatment may relate to the administration of a pharmaceutical composition of the present invention to a subject.

Suitably, the present invention provides a method of treatment comprising:
  (i) providing a sample comprising a starting population of cells;
  (ii) depleting said starting population of cells which express a target antigen;
  (iii) introducing into a cell in the depleted starting population a nucleic acid sequence which encodes a CAR or transgenic TCR against the target antigen; and
  (iv) administering the cells from (iii) to a subject.

Suitably, the method may additionally comprise a cell expansion step before administration to the patient e.g. the cells may be cultured before administration to the patient.

The genetically modified cells or pharmaceutical composition of the present invention may be used for the treatment and/or prevention of a cancerous disease, such as a haematological malignancy, bladder cancer, breast cancer, colon cancer, endometrial cancer, kidney cancer (renal cell), lung cancer, melanoma, pancreatic cancer, prostate cancer and thyroid cancer, cancers of the oral cavity and pharynx which includes cancer of the tongue, mouth and pharynx; cancers of the digestive system which includes oesophageal, gastric and colorectal cancers; cancers of the liver and biliary tree which includes hepatocellular carcinomas and cholangiocarcinomas; cancers of the respiratory system which includes bronchogenic cancers and cancers of the larynx; cancers of bone and joints which includes osteosarcoma; cancers of the skin which includes melanoma; breast cancer; cancers of the genital tract which include uterine, ovarian and cervical cancer in women, prostate and testicular cancer in men; cancers of the renal tract which include renal cell carcinoma and transitional cell carcinomas of the utterers or bladder; brain cancers including gliomas, glioblastoma multiforme and medullobastomas; cancers of the endocrine system including thyroid cancer, adrenal carcinoma and cancers associated with multiple endocrine neoplasm syndromes; and cancers of other and unspecified sites including neuroblastoma.

Suitably, the genetically modified cells or pharmaceutical composition of the present invention may be used for the treatment and/or prevention of a haematological malignancy.

As used herein, "haematological malignancy" refers to a cancer which affects the blood and lymph system and includes leukaemia, lymphoma, myeloma and related blood disorders.

Suitably, the genetically modified cells or pharmaceutical composition of the present invention may be used for the treatment and/or prevention of a haematological malignancy.

Suitably, the genetically modified cells or pharmaceutical composition of the present invention may be used in the treatment and/or prevention of leukaemias both acute and chronic, myeloid or lymphoid including: acute lymphoblastic leukaemia (ALL), acute myeloid leukaemia (AML), acute premyelocytic leukaemia (APL), and B- or T-cell acute lympoblastic leukaemia (B-ALL or T-ALL respectively), chronic lymphocytic leukaemia (CLL), chronic myeloid leukaemia (CML), chronic myelomonocytic leukaemia (CMML), hairy cell leukaemia (HCL) and large granular lymphocytic leukaemia (LGLL); lymphomas including Hodgkin's lymphoma and non-Hodgkin lymphoma (NHL), both Low-grade NHL and High-grade NHL; myeloma (Multiple Myeloma (MM)), including: smouldering or asymptomatic myeloma and symptomatic myeloma and other conditions related to blood cancer such as monoclonal gammopathy of undetermined significance (MGUS), myelodysplastic sydromes (MDS), solitary plasmacytoma, and myeloproliferative neoplasms (MPN), including essential thrombocythaemia (ET), myelofibrosis (MF), and polycythaemia vera (PV).

Suitably, the genetically modified cells or pharmaceutical composition of the present invention may be used in the treatment and/or prevention of a T cell lymphoma. Suitably, the genetically modified cells or pharmaceutical composition of the present invention may be used in the treatment and/or prevention of a T cell leukaemia.

A method for treating a T-cell lymphoma and/or leukaemia relates to the therapeutic use of an genetically modified cell of the invention. The genetically modified cell may be administered to a subject having an existing disease of T-cell lymphoma and/or leukaemia in order to lessen, reduce or improve at least one symptom associated with the disease and/or to slow down, reduce or block the progression of the disease.

Suitably, the method of the present invention may be used for the treatment of any lymphoma and/or leukaemia associated with the clonal expansion of a cell expressing a T-cell receptor (TCR) comprising a β constant region. As such the present invention may relate to a method for treating a disease which involves malignant T cells which express a TCR comprising a TRBC such as TRBC1 or TRBC2.

Suitably, the method of the present invention may be used to treat a T-cell lymphoma in which the malignant T-cell expresses a TCR comprising a TRBC. "Lymphoma" is used herein according to its standard meaning to refer to a cancer which typically develops in the lymph nodes, but may also affect the spleen, bone marrow, blood and other organs. Lymphoma typically presents as a solid tumour of lymphoid cells. The primary symptom associated with lymphoma is lymphadenopathy, although secondary (B) symptoms can include fever, night sweats, weight loss, loss of appetite, fatigue, respiratory distress and itching.

The method of the present invention may be used to treat a T-cell leukaemia in which the malignant T-cell expresses a TCR comprising a TRBC. "Leukaemia" is used herein according to its standard meaning to refer to a cancer of the blood or bone marrow.

The following is an illustrative, non-exhaustive list of diseases which may be treated by the method of the present invention.

Suitably, the T-cell lymphoma or leukaemia may be peripheral T-cell lymphoma, not otherwise specified (PTCL-NOS). Suitably, the T-cell lymphoma or leukaemia may be angio-immunoblastic T-cell lymphoma (AITL). Suitably, the T-cell lymphoma or leukaemia may be anaplastic large cell lymphoma (ALCL). Suitably, the T-cell lymphoma or leukaemia may be enteropathy-associated T-cell lymphoma (EATL). Suitably, the T-cell lymphoma or leukaemia may be hepatosplenic T-cell lymphoma (HSTL). Suitably, the T-cell lymphoma or leukaemia may be extranodal NK/T-cell lymphoma nasal type. Suitably, the T-cell lymphoma or leukaemia may be cutaneous T-cell lymphoma (CTCL). Suitably, the T-cell lymphoma or leukaemia may be primary cutaneous (ALCL). Suitably, the T-cell lymphoma or leukaemia may be T cell prolymphocytic leukaemia. Suitably, the T-cell lymphoma or leukaemia may be T-cell acute lymphoblastic leukaemia.

Treatment with the genetically modified cells of the present invention or pharmaceutical composition according to the present invention may help prevent the escape or release of tumour cells which often occurs with standard approaches.

The term "treat/treatment/treating" refers to administering an genetically modified cell, population of genetically modified cells, or pharmaceutical composition according to the present invention to a subject having an existing disease or condition in order to lessen, reduce or improve at least one symptom associated with the disease and/or to slow down, reduce or block the progression of the disease.

Reference to "prevention"/"preventing" (or prophylaxis) as used herein refers to delaying or preventing the onset of the symptoms of the disease. Prevention may be absolute (such that no disease occurs) or may be effective only in some individuals or for a limited amount of time.

In a preferred embodiment of the present invention, the subject of any of the methods described herein is a mammal, preferably a cat, dog, horse, donkey, sheep, pig, goat, cow, mouse, rat, rabbit or guinea pig. Preferably the subject is a human.

Administration

The administration of the pharmaceutical composition can be accomplished using any of a variety of routes that make the genetically modified cells comprised in the pharmaceutical composition bioavailable to the subject. For example, the composition can be administered by oral and parenteral routes, intraperitoneally, intravenously, subcutaneously, transcutaneously, intramuscularly, via local delivery for example by catheter or stent.

Suitably, the genetically modified cell according to the invention or the pharmaceutical composition according to the invention is administered intravenously.

Those skilled in the art will appreciate, for example, that route of delivery (e.g., oral vs intravenous vs subcutaneous, etc.) may impact dose amount and/or required dose amount may impact route of delivery. For example, where particularly high concentrations of an agent within a particular site or location are of interest, focused delivery may be desired and/or useful. Other factors to be considered when optimizing routes and/or dosing schedule for a given therapeutic regimen may include, for example, the disease being treated (e.g., type or stage, etc.), the clinical condition of a subject (e.g., age, overall health, etc.), the presence or absence of combination therapy, and other factors known to medical practitioners.

The dosage is such that it is sufficient to stabilise or improve symptoms of the disease.

Typically, a physician will determine the actual dosage which will be most suitable for an individual subject and it will vary with the age, weight and response of the particular patient. The dosage is such that it is sufficient to reduce or deplete the number of cells expressing the target antigen.

Use

The present invention also provides a pharmaceutical composition or population of genetically modified cells according to the invention for use in treating disease. The pharmaceutical composition or population of genetically modified cells may be any as defined above.

The present invention also relates to the use of a population of genetically modified cells of the present invention as defined above in the manufacture of a medicament for the treatment of a disease.

Kits

The present invention also provides a kit which comprises:
 (i) a first nucleic acid sequence which encodes a CAR or a transgenic TCR; and
 (ii) means for depleting cells expressing the target antigen for the CAR or transgenic TCR.

As used herein "means for depleting cells expressing the target antigen" refers to any product known in the art suitable for removing or separating specific cells from a mixed population of cells.

Suitably, the kit may comprise antibodies specific for the target antigen.

Suitably, the kit may comprise a depleting antibody. A "depleting antibody" is an antibody which binds to an antigen present on a target cell and mediates death of the target cell. The administration of a depleting antibody to a population of cells therefore results in reduction/decrease in the number of cells in the population which express the target antigen.

Suitably, the kit may comprise an antibody-coated solid matrix. Cells expressing the target antigen may be depleted by adsorption to the antibody-coated solid matrix.

Suitably, the kit may comprise a fluorescent antibody specific for the target antigen. A cell comprising the target antigen may be isolated by flow cytometry.

Suitably, the kit may comprise immunomagnetic products, i.e. antibodies specific for the target antigen attached to magnetic nanoparticles or beads.

The invention will now be further described by way of Examples, which are meant to serve to assist one of ordinary skill in the art in carrying out the invention and are not intended in any way to limit the scope of the invention.

EXAMPLES

Example 1—Manufacture of a Genetically Modified Autologous Cellular Gene Therapy Drug Product for the Treatment of T Cell Lymphoma The standard CAR-T cell manufacturing process can be summarised by the five stages below. Introducing a TRBC1+ cell depletion step prior to the activation step has been assessed.
1. Isolation of PBMCs from leukapheresate to provide the starting material for the manufacturing process.
2. Activation of patient-derived T cells using anti-CD3 and anti-CD28 monoclonal antibodies in the presence of cytokines.
3. Transduction of patient-derived T cells with retroviral supernatant.
4. Expansion of the transduced T cells using cytokines (Drug Substance [DS]).
5. Formulation and filling of cells into bag and cryopreservation (DP).

Proof of principle (PoP) development experiments, utilising MACS microbeads and columns (Miltenyi) to capture TRBC1+ cells labelled with anti-TRBC1 antibody, demonstrated efficient sorting of TRBC1+ and TRBC1− cells as well as feasibility for manufacture. An additional, surprising, outcome was that TRBC1+ cells proved refractory to transduction at the low multiplicity of infections (MOIs) used (possibly due to receptor interference, as the virions may bind the cells via the TCR rather than the RD114 receptor). In summary, incorporating the depletion step resulted in a more robust process (more reproducible transduction efficiency and residual TRBC1+ T cell levels in the DP) with enhanced safety (minimal/undetectable levels of transduced TRBC1+ T cells in DS/DP).

Experimental Approach

Optimal TRBC1+ cell labelling and depletion/sorting conditions were established using Ms (mouse) anti-TRBC1 (JOVI-1) antibody (unconjugated and biotinylated) in conjunction with MACS microbeads (anti-Ms and anti-biotin) and columns (not discussed in this report, but exemplified in FIG. 1). A series of PoP development experiments, performed on healthy donor leukapheresates at different scales, went on to evaluate incorporating the depletion step into the CAR-T cell manufacturing process, including adaption into the automated CliniMACS Prodigy CAR-T cell manufacturing protocol for GMP compliance. Data were collected to determine the efficiency of the depletion and to assess transduction efficiency, cell growth and viability as well as memory and exhaustion phenotypes at the end of the process. In addition, cytokine analysis performed on the culture media provided information on the release of IL-2, TNFα, IFNγ and Granzyme B, associated with T cell activation and cytotoxicity. Lastly, cytotoxicity/cytokine release assays enabled functional evaluation of the CAR-T cells produced. This involved co-culturing the CAR-T cells with TRBC1+ Raji cells, a lymphoblast-like tumour cell line transduced to express the TRBC1 tumour antigen. FACS to determine target cell killing after 48 h and cytokine release analysis provided a measure of CAR-T cell cytotoxicity and potency.

Protocol Overview

Small and large scale experiments depleted TRBC1+ cells from $1.5 \times 10^7$ to $7 \times 10^8$ cells and transduced $0.3 \times 10^6$ to $1.4 \times 10^8$ T cells. In addition, some large scale experiments were automated, from day 0, on the CliniMACS Prodigy. All experiments followed the same basic protocol. On Day −1, frozen donor leukapheresis samples were thawed and incubated overnight in cell culture media supplemented with serum to recover.

On Day 0, TRBC1+ cells were depleted/sorted on MACS LS columns after labelling with 0.125 µg anti-TRBC1 antibody (unconjugated or biotinylated) per $10^6$ cells and then 10 µl MACS microbeads (anti-Ms or anti-biotin) per $10^7$ cells. FACS to determine TRBC1+ cell content in pre and post depleted/sorted samples provided an evaluation of the sorting efficiency. Cells from the sorted and unsorted subsets were seeded at $1 \times 10^6$ cells/ml in cell culture media supplemented with serum and IL-7 and IL-15 and TransAct reagents (Miltenyi) added to activate T cells.

Depletion of Cells Expressing a Target Antigen

Figure 2:
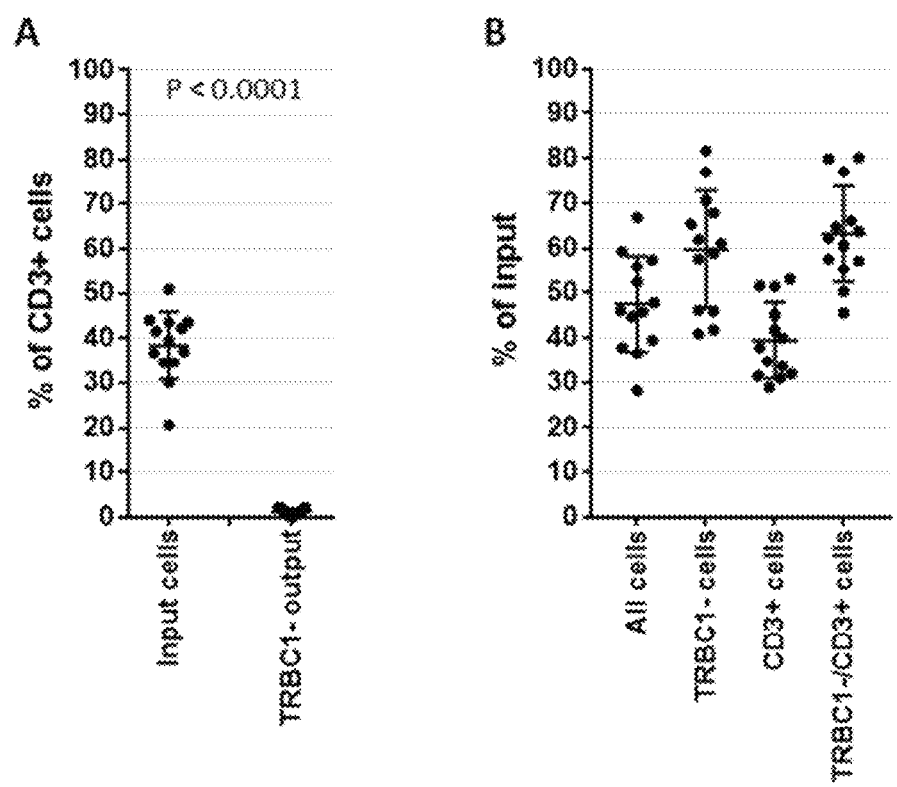
FIG. 2—Graphs showing TRBC1 depletion efficiency. Averaged data showing (A) comparison of TRBC1+ cell content pre (input) and post (TRBC1− output) depletion. (B) The percentage of input cell subsets recovered from the depletion (TRBC1− output) (n=13).

The plots in FIG. 1 show TRBC1+ cell content in the non depleted input, TRBC1-output (depleted column flow through) and TRBC1+ output (column captured) samples from depletions performed on $2.1 \times 10^7$ cells. Data shown in FIG. 2 demonstrates the effectiveness of the initial depletion step, with <1.2% TRBC1+ cells measured in the T cell population after depletion and >60% of the TRBC1− T cell input recovered (TRBC1−/CD3+ cells).

CAR Transduction

On Day 2 (48 h post activation), cells were transduced at specified MOI's with an anti-TRBC1 CAR vector, a control CAR1 vector, or a control CAR2 vector using either Retronectin (Takara) or Vectofusin (Miltenyi) transduction enhancers. Cells were allowed to transduce overnight before being washed, reseeded in fresh cell culture media supplemented with serum and IL-7 and IL-15 and then cultured to day 6-10.

Figure 3:
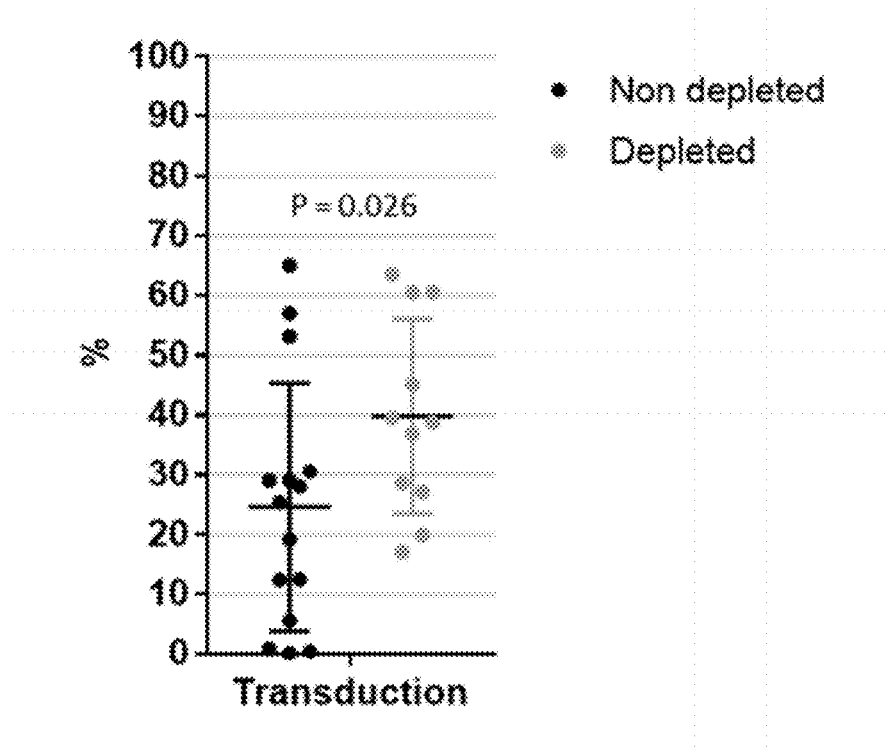
FIG. 3—Graph showing a comparison of TRBC1 CAR transduction. Data showing the levels of transduction (marker+/CD3+ cells), achieved using retronectin, at the end of the process (non depleted n=15; depleted n=11; 8 matched pairs. Paired t-test n=8).
Figure 4:
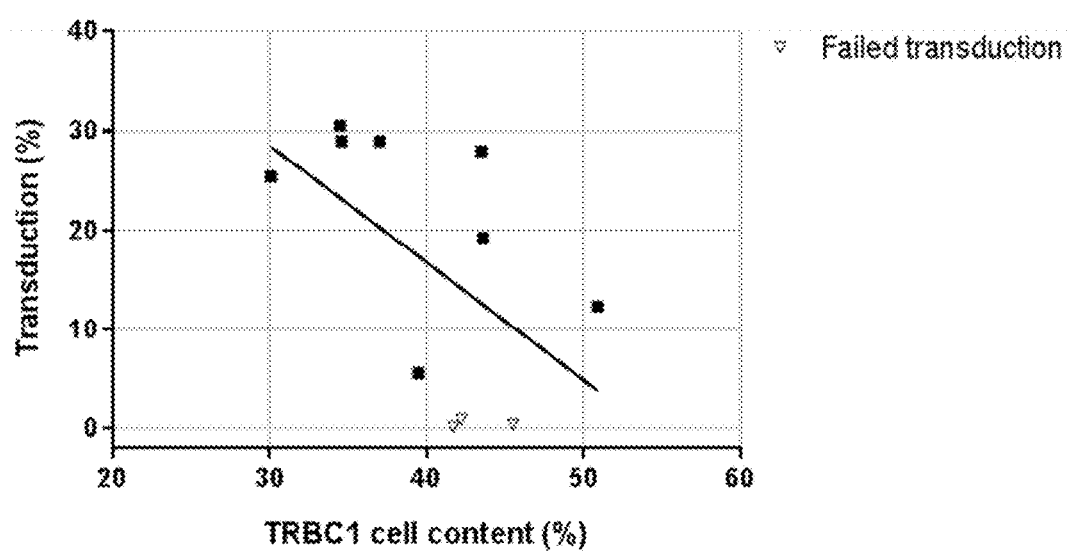
FIG. 4—Graph showing transduction efficiency v TRBC1+ cell content. Data to correlate transduction in non depleted cells with TRBC1+ cell content at the time of transduction (n=11). TRBC1+ cell content for failed transductions indicated.

Unexpectedly, using depleted cells for CAR-T cell production resulted in a significant improvement in the levels of anti-TRBC1 CAR-Transduction compared to non-depleted cells (24.5% vs 39.8%)(FIG. 3). Three experiments using non-depleted cells actually failed to transduce with the anti-TRBC1 CAR, despite successful parallel transductions using depleted cells or a control CAR (Table 1). Interestingly, in all three the percentage of TRBC1+ cells in the starting material was high (>40%), suggesting a further unexpected advantage of performing the depletion. When plotting the transduction efficiency against TRBC1 content for non depleted samples, a weak correlation is indeed observed between transduction efficiency and TRBC1+ cell content at the time of transduction (FIG. 4).

TABLE 1

Experiments in which anti-TRBC1 CAR-Transduction failed.

| Experiment | % of TRBC1+ cells | TRBC1 CAR-Transduction % in non-depleted sample | Parallel transduction % in non-depleted sample with control (CAR1 or CAR2) | Parallel transduction % in TRBC1+ depleted sample |
| --- | --- | --- | --- | --- |
| 1 | 45.5% | 0.38% | Not done | Not done |
| 2 | 42.2% | 0.87% | 15.1% | Not done |
| 3 | 41.7% | 0.11% | 28.5% | Not done |

Cell Purity

Analysis performed at the end of the manufacturing process consisted of FACS to determine TRBC1+ cell content and % transduction efficiency along with exhaustion (PD1, Lag3 and Tim3 expression) and memory phenotypes (CCR7 against CD45RA expression) in the CD3+ and CD8+ cell subsets. IL-2, TNFα, IFNγ and Granzyme B release in the culture media was also measured, using the SimplePlex assay. Cell counts to assess expansion of the culture were also performed.

Figure 5:
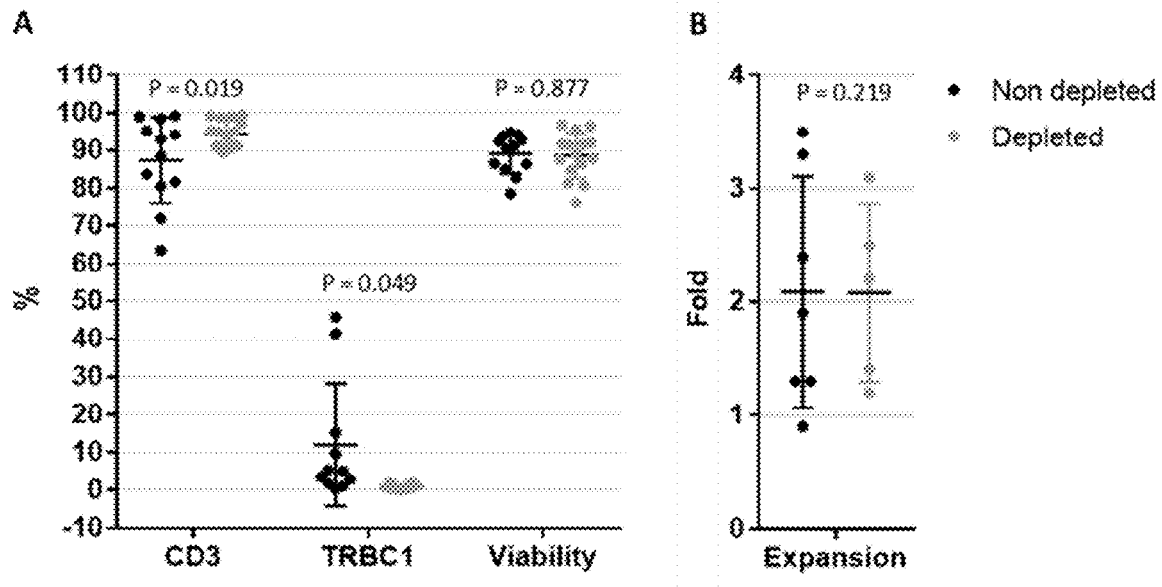
FIG. 5—Graphs showing comparisons of the TRBC1 CAR-Transduction process. Data showing (A) final CD3 and TRBC1 cell content with cell viability (non depleted n=12; depleted n=15; 12 matched pairs. Paired t-test n=12). (B) Culture expansion post transduction (non depleted n=7; depleted n=5; 4 matched pairs. Paired t-test n=4).

Cell purity at the end of the production process was less variable and significantly improved when depleted cells were used compared to non-depleted (94.5% vs 87.4% CD3+)(FIG. 5A). At this point, culture expansion and viability were comparable for both depleted and non depleted cells, but expansion was also less variable using depleted cells (FIGS. 5B and 5A respectively). When non depleted cells were used TRBC1+ cell content at the end of the process remained, on average, significantly higher compared to the depleted cells (>12% vs <1%)(FIG. 5A). This was surprising, expectations were that killing from the anti-TRBC1 CAR+ cells would efficiently deplete the TRBC1+ cells and this data highlights the potential risk of transduced malignant cells in the final drug product if the initial depletion is not performed.

Phenotypic Analysis

Figure 6:
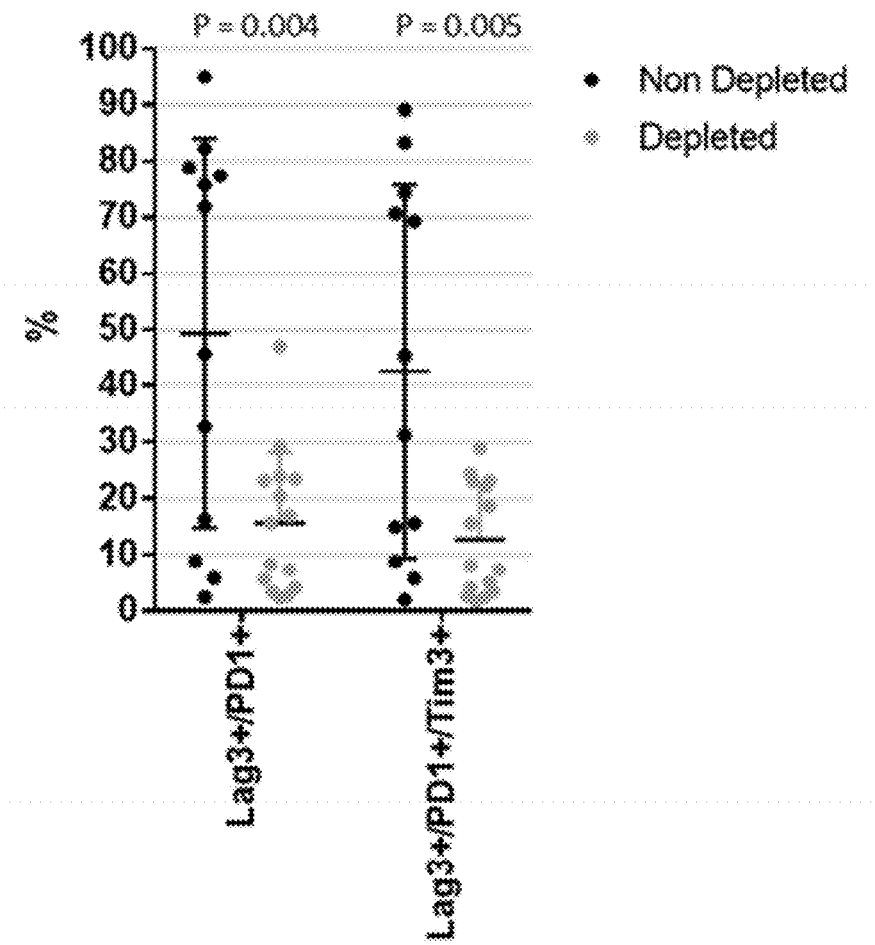
FIG. 6—Graph showing exhaustion phenotypes in the transduced (marker+) CD8+ T cell subset. Averaged data to show the percentage of cells expressing multiple exhaustion markers (Lag3, PD1 and Tim3) (non depleted n=12; depleted n=15; 12 matched pairs. Paired t-test n=12).
Figure 7:
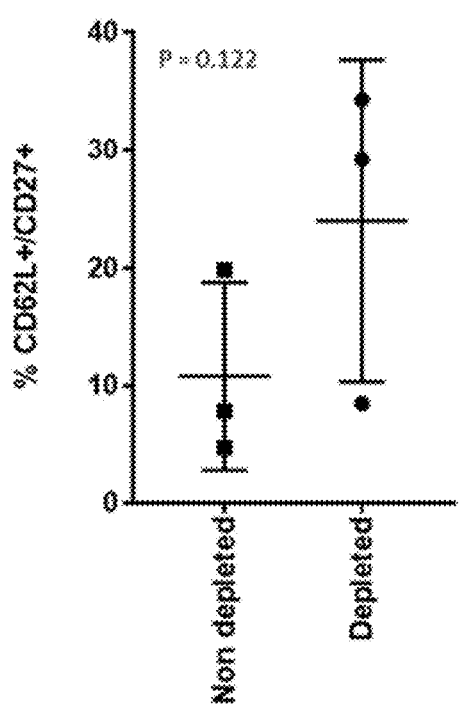
FIG. 7—Bar chart and graph showing memory phenotypes in the transduced CD8+ T cell subset. Averaged data showing enhanced phenotyping of the naïve cell subset (CCR7+/CD45RA+) to identify CD62L+/CD27+ cells and further discriminate undifferentiated cells (n=3).

Phenotypic analysis also identified significantly higher co-expression of PD1, Lag3 and Tim3 exhaustion markers in the transduced T cells when using non-depleted cells (FIG. 6). Corresponding memory phenotypes, based on CCR7, CD45RA, CD27 and CD62L expression indicated a more differentiated phenotype when non-depleted cells are used (FIG. 7).

In addition, cytokine analysis on the final cultures during CAR-T cell production revealed consistently low levels of IL-2, TNFα, IFNγ and Granzyme B with depleted cells, but proved highly variable with non-depleted cells and, on average, significantly higher for Granzyme B and IL-2 (FIG. 8). Cytotoxicity data (cell killing and cytokine release) data also suggest that CAR-T cells derived from depleted cells are more consistent on average, and demonstrate improved cell killing ability as supported by the overall trends and the statistically significant differences in the release IL-2 and TNF-a (FIGS. 9 and 10).

Figure 11:
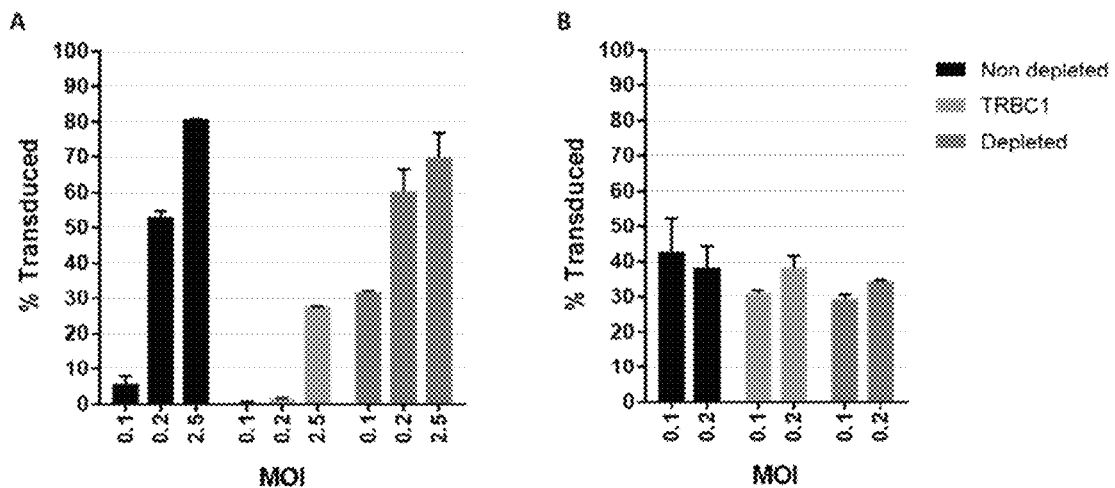
FIG. 11—Bar chart showing TRBC1+ cell transduction. Data showing comparative transduction of non-depleted, TRBC1+ and depleted cells at different MOIs, (A) with the TRBC1 CAR, (B) with a control CAR (n=1; average of duplicate wells).

Transduction and expansion of TRBC1+ selected cells, retained from the depletion process, was also studied. Surprisingly, when transduced at the low MOIs used for our CAR-T cell manufacture, TRBC1+ cells failed to transduce successfully with the anti-TRBC1 CAR (<2%), shown to be CAR specific by efficient transduction of these cells with a control CAR (>30%) that does not target TRBC1 or T cells generally (exemplified in FIG. 11). Specifically addressing this phenomena, one small scale experiment showed that anti-TRBC1 CAR-Transduction could be achieved in these cells by dramatically increasing the MOI (>10 fold), albeit with comparatively low efficiency to depleted cells (27.7% v 70%) (FIG. 11). Receptor interference could be a possible cause, as the virions may bind to cells via the TCR as well as the RD114 receptor, with high MOIs overcoming this by saturating all of the receptors.

Summary and Conclusions

This work establishes the feasibility of depleting cells which express a target antigen as part of the genetically modified cell manufacturing process without impairing the ability to activate, transduce and expand the depleted cells in culture.

Instead, analyses described herein show that depleting TRBC1+ cells offers distinct advantages for the production of a cellular gene therapy drug product comprising T cells retrovirally transduced to express an anti-TRBC1 specific CAR; improved transduction and cell purity, with less exhausted CAR-T cells that are, potentially, less differentiated than those produced from non depleted cells.

In addition, functional analyses suggest improved consistency and potency in anti-TRBC1 CAR-T cell cytotoxicity when produced from depleted cells.

Surprisingly, an added safety benefit for the manufacture of a cellular gene therapy drug product comes from the observation that TRBC1+ cells failed to transduce with the anti-TRBC1 CAR when low MOIs for transduction were used. Expectations are that TRBC1+ tumour cells, even if present in the leukapheresate, will not transduce effectively with the anti-TRBC1 CAR retrovirus at the MOIs optimised for CAR-T cell manufacture.

Example 2—Manufacture of a Genetically Modified Cellular Gene Therapy Drug Product for the Treatment of B Cell Malignancies In healthy donors usually a small percentage of B cells are observed in the starting leukapheresate material and this population usually disappears towards the end of the CAR T cell manufacturing process, following transduction.

A series of experiments were performed using four healthy donors. For each donor, B cells were depleted using CD19+ microbeads and MACS selection column. The CD19− (depleted) leukapheresate was then cultured following the standard manufacturing process described below. For each donor, a non-depleted condition was used as a control.

Figure 12:
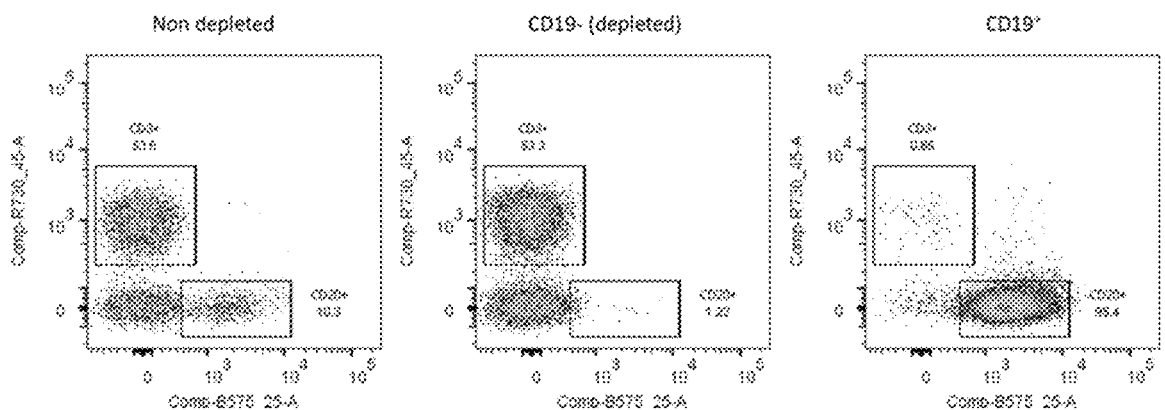
FIG. 12—FACS plots showing CD19+ cells depletion. Representative depletion performed using the CD19+ microbeads and MACS selection column. The plots show the non depleted input, the CD19− (depleted column flow through) and CD19+ output (column captures) samples.
Figure 13:
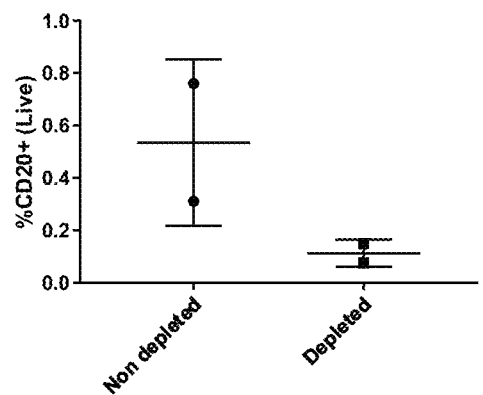
FIG. 13—Graph showing the percentage of B cells (i.e. CD20+) in culture at day 6 (D6) of the manufacturing process. Even in the non depleted culture, low % of live CD20+ cells (i.e. <1%) were detected at the end of the culture. N=2

An example of B cells depletion is shown in FIG. 12. B cells were stained with a PE-conjugated CD20 antibody. Staining with a CD19 antibody was not feasible, as blocking of the CD19 binding site was observed following selection with the CD19 microbeads.

Data was collected at the end of the manufacturing process to assess transduction efficiency. In addition, cytokine analysis performed on the culture media provided information on the release of IL-2, TNFα, IFNγ and Granzyme B, associated with T cell activation and cytotoxicity.

Protocol Overview

Experiments were performed in 24 well plates. On Day −1, frozen donor leukapheresate samples were thawed and incubated overnight in cell culture media supplemented with serum to recover. On Day 0, CD19+ cells were depleted on MACS LS columns after labelling with anti-CD19 microbeads. In one of the experiments, B cells were depleted one week before the start of the experiment and CD19 depleted and non-depleted leukapheresate samples were frozen and kept in liquid nitrogen before being thawed for the experiment. FACS was performed using anti-CD20 antibody to determine the B cell content in pre and post depleted/sorted samples. Cells from both conditions were seeded at $1 \times 10^6$ cells/ml in cell culture media supplemented with serum and IL-7 and IL-15 and TransAct reagents (Miltenyi) added to activate T cells.

On Day 2 cells at all conditions were then transduced ($0.3 \times 10^6$ cells/well) at MOI 0.2 with an anti-CD19/22 CAR (also referred to an CD19/22 CAR) using Retronectin (Takara) transduction enhancers. Cells were allowed to transduce overnight before being washed, reseeded in fresh cell culture media supplemented with serum and IL-7 and IL-15 and then cultured to day 7.

Results

Figure 14:
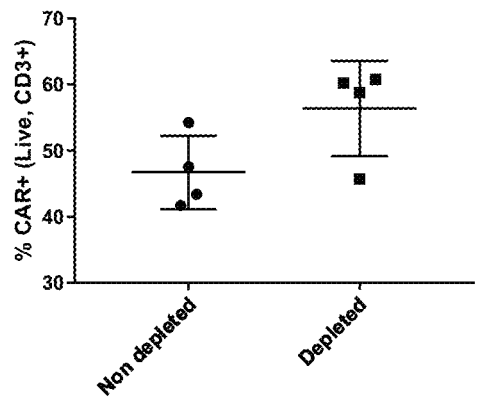
FIG. 14—Graph showing the transduction efficiency at the end of the culturing period day 7 (D7). % CAR+ cells were measured from live, CD3+ cells. Higher transduction was observed in CD19 depleted cells, compared to the non depleted control. N=4.

Transduction efficiency was measured for both depleted and non-depleted cultures on the last day of culture (day 7). As shown in FIG. 14, higher transduction was observed when the B cells depletion step was performed at the start of the manufacturing process.

Figure 15:
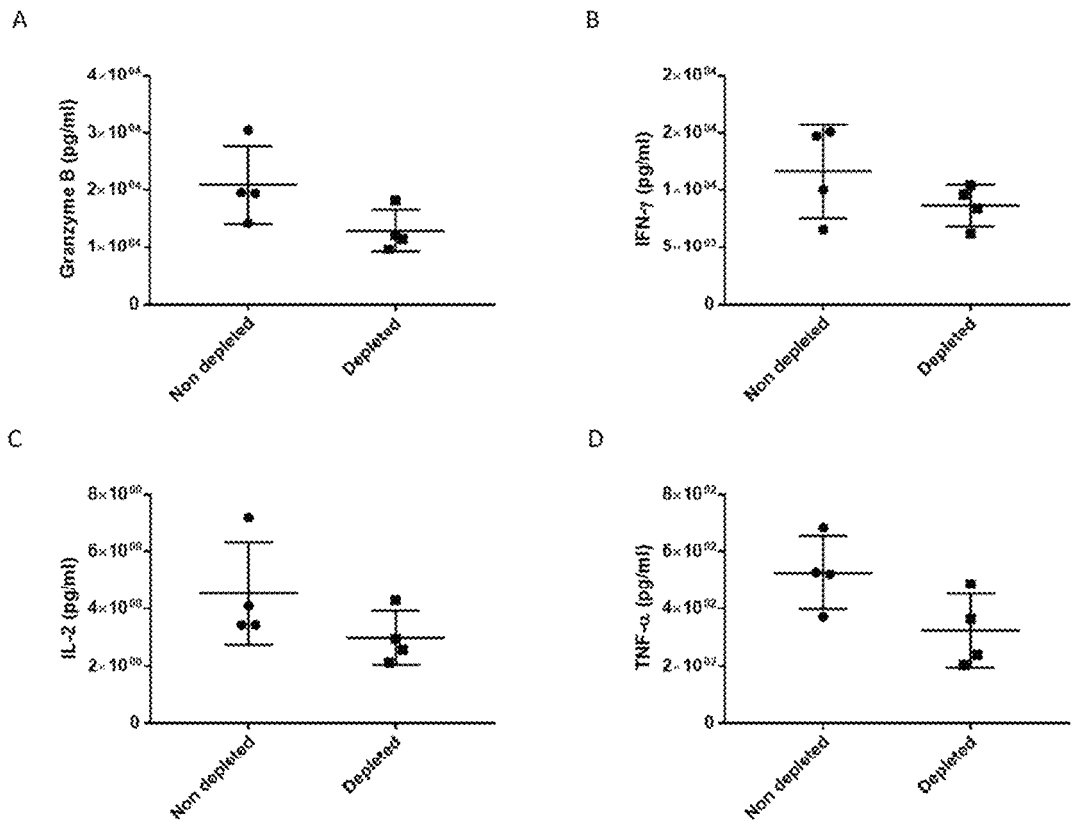
FIG. 15—Graphs showing cytokines released into the culture media. These end of process data show concentrations of (A) Granzyme B, (B) IFN-γ, (C) IL-2 and (D) TNF-α released into the culture. For all cytokines, the lowest concentration was observed in depleted samples compared to non depleted. N=4.

At the end of the 7 days in culture, supernatant was harvested for each condition and analysed for the presence of cytokines. As shown in FIG. 15, low concentrations of IL-2, TNFα, IFNγ and Granzyme B were observed in depleted cultures, while values were found to be more variable and consistently higher in non-depleted cultures, suggesting B cells killing occurring during the manufacturing process.

Summary and Conclusions

The presence of B cells in the starting material of a cell therapy which targets B cells could negatively affect transduction efficiency during the manufacturing process. Furthermore, higher concentrations of cytokines in the culture supernatant were observed in non-depleted samples, suggesting killing occurring during the manufacturing process when B cells are present. This could potentially affect CAR T cells performance and persistence once infused in vivo.

Thus, the addition of a B cells depletion step at the start of the manufacturing process could significantly improve the quality of the final product and robustness of the process, as well as ensuring safety minimising the risk of transduction of malignant B cells if the patient is suffering from a haematological malignancy.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

The invention claimed is:

1. A method of preparing a population of genetically modified T cells which comprise a chimeric antigen receptor (CAR) or a transgenic T-cell receptor (TCR) comprising:
   providing a starting population of T cells,
   depleting said starting population of T cells which express a target antigen, and
   introducing into the T cells in the depleted starting population a nucleic acid sequence which encodes a CAR or transgenic TCR against the target antigen,
   wherein the target antigen is TCR beta constant region 1 (TRBC1) or TCR beta constant region 2 (TRBC2), and
   wherein said genetically modified T cells are less exhausted compared with genetically modified T cells prepared without depleting said starting population of T cells which express the target antigen of the CAR or transgenic TCR.

2. A method according to claim 1, wherein the target antigen is TCR beta constant region 1 (TRBC1).

3. A method according to claim 1, wherein the target antigen is TCR beta constant region 2 (TRBC2).

4. A method according to claim 1, wherein fewer than 10% of the genetically modified T cells express the target antigen of the CAR or transgenic TCR.

5. A method according to claim 1, wherein fewer than 5% of the genetically modified T cells express the target antigen of the CAR or transgenic TCR.

6. A method according to claim 1, wherein less than 1% of the genetically modified T cells express the target antigen of the CAR or transgenic TCR.

7. A method according claim 1, wherein the nucleic acid sequence which encodes the CAR or transgenic TCR is introduced into the cell by transduction and wherein the multiplicity of infection is about 0.1 to 1.2 sufficient to transduce cells which do not express the target antigen and insufficient to transduce cells which express the target antigen.

* * * * *

UNITED STATES PATENT AND TRADEMARK OFFICE
CERTIFICATE OF CORRECTION

PATENT NO.         : 11,903,967 B2
APPLICATION NO.    : 16/188185
DATED              : February 20, 2024
INVENTOR(S)        : Martin Pulé et al.

It is certified that error appears in the above-identified patent and that said Letters Patent is hereby corrected as shown below:

On the Title Page

Below "Item (65)" insert -- (30) Foreign Application Priority Data Jan. 09, 2018 (GB) ...........................1800298.0 --.

In the Claims

At Column 34, Line 30, "according" should be -- according to --.

Signed and Sealed this
Third Day of September, 2024

Katherine Kelly Vidal
Director of the United States Patent and Trademark Office